(12) United States Patent
de Vaan et al.

(10) Patent No.: US 11,793,484 B2
(45) Date of Patent: Oct. 24, 2023

(54) METHOD, DEVICE AND SYSTEM FOR INTRACAVITY PROBE PROCEDURE PLANNING

(71) Applicant: 3mensio Medical Imaging B.V., Bilthoven (NL)

(72) Inventors: Jan Anne Niels de Vaan, Houten (NL); Martijn Lambertus Laurentius Chatrou, Son en Breugel (NL)

(73) Assignee: 3mensio Medical Imaging B.V., Bilthoven (NL)

( * ) Notice: Subject to any disclaimer, the term of this patent is extended or adjusted under 35 U.S.C. 154(b) by 811 days.

(21) Appl. No.: 16/694,812

(22) Filed: Nov. 25, 2019

(65) Prior Publication Data

US 2020/0170617 A1 Jun. 4, 2020

Related U.S. Application Data

(60) Provisional application No. 62/774,800, filed on Dec. 3, 2018.

(51) Int. Cl.
*G06T 7/00* (2017.01)
*A61B 8/12* (2006.01)
(Continued)

(52) U.S. Cl.
CPC ............... *A61B 8/12* (2013.01); *A61B 34/10* (2016.02); *A61B 34/20* (2016.02); *G06T 7/0012* (2013.01);
(Continued)

(58) Field of Classification Search
CPC .............................. A61B 8/12; G06T 7/0012
See application file for complete search history.

(56) References Cited

U.S. PATENT DOCUMENTS

| | | | |
|---|---|---|---|
| 9,008,386 | B2 | 4/2015 | Verstraeten et al. |
| 2009/0162820 | A1 | 6/2009 | Tada et al. |

(Continued)

FOREIGN PATENT DOCUMENTS

EP 2538398 A1 12/2012

OTHER PUBLICATIONS

"American Society of Echocardiography and the Society of Cardiovascular Anesthesiologists" Cahalan et al. (Anesth Analg. Jun. 2002; 94(6):1384-8).

(Continued)

*Primary Examiner* — Edward Park
(74) *Attorney, Agent, or Firm* — GORDON & JACOBSON, P.C.

(57) ABSTRACT

A method (and imaging system) for planning a medical intervention on patient is provided that involves an intracavity probe and an imaging dataset of the patient. A view-type is selected from a defined set of view-types. A virtual field of view of the intracavity probe corresponding to the selected view-type is determined. A virtual intracavity image is rendered for display, wherein the virtual intracavity image is based upon the imaging dataset of the patient and the virtual field of view of the intracavity probe. The virtual field of view can be based upon segmentation of an intracavity path of the probe and at least one anatomical structure or possibly based on user input. In embodiments, the virtual field of view can be based upon probe parameters computed in accordance with a pre-defined set of rules for the selected view-type. The probe parameters can be computed by evaluation of a cost function expressed by the pre-defined set of rules for the selected view-type. Other aspects are described and claimed.

18 Claims, 19 Drawing Sheets

(51) Int. Cl.
*A61B 34/10* (2016.01)
*A61B 34/20* (2016.01)

(52) U.S. Cl.
CPC ... *A61B 2034/101* (2016.02); *A61B 2034/107* (2016.02); *A61B 2034/2046* (2016.02); *G06T 2207/10072* (2013.01)

(56) References Cited

U.S. PATENT DOCUMENTS

| | | | |
|---|---|---|---|
| 2013/0218157 A1* | 8/2013 | Callas | A61B 18/14 606/41 |
| 2018/0350064 A1* | 12/2018 | Man | A61B 8/483 |
| 2019/0357987 A1* | 11/2019 | Harks | A61B 34/20 |
| 2020/0037983 A1* | 2/2020 | Poland | A61B 8/14 |
| 2020/0054399 A1* | 2/2020 | Duindam | A61B 34/20 |
| 2020/0170617 A1* | 6/2020 | de Vaan | G06T 19/003 |
| 2020/0323514 A1* | 10/2020 | Thienphrapa | A61B 8/5223 |

OTHER PUBLICATIONS

"Computed Tomography for Structural Heart Disease and Interventions", Thériaultlauzier et al., Interventional Cardiology Sep. 2015; 10(3): 149-154.

"Coordinate descent algorithms", Wright Mathematical programming, Jun. 2015, vol. 151.

"Esophagus Segmentation from 3D CT Data Using Skeleton Prior-Based Graph Cut", Grosgeorge et al., Comput Math Methods Med. 2013; 2013: 547897.

"Four-Chamber Heart Modeling and Automatic Segmentation for 3D Cardiac CT Volumes Using Marginal Space Learning and Steerable Features", Zhen et al, IEEE Trans Med Imaging Nov. 2008;27(11):1668-81.

"Guidelines for performing a comprehensive transesophageal echocardiographic examination: recommendations from the American Society of Echocardiography and the Society of Cardiovascular Anesthesiologists", Hahn et al, Anesth Analg. Jan. 2014;118(1):21-68.

"Intracardiac Echocardiography in Structural Heart Disease Interventions", M. Alkhouli et al, JACC: Cardiovascular Interventions, vol. 11, issue 21, Nov. 2018.

"Mitral Annular Evaluation with CT in the Context of Transcatheter Mitral Valve Replacement", Blanke et al, JACC Cardiovasc Imaging May 2015;8(5):612-615.

"Percutaneous mitral repair with the MitraClip system: safety and midterm durability in the initial EVEREST (Endovascular Valve Edge-to-Edge Repair Study) cohort", Feldman et al, J Am Coll Cardiol. Aug. 18, 2009;54(8):686-94.

"Quantitative multi-slice computed tomography assessment of the mitral valvular complex for transcatheter mitral valve interventions part 1: systematic measurement methodology and inter-observer variability", Thériault-Lauzier et al., EuroIntervention. Oct. 10, 2016;12(8): e1011-e1020.

"Role of echocardiography for catheterbased management of valvular heart disease", Shiota et al., Journal of Cardiology 69 (2017) 66-73.

\* cited by examiner

METHOD, DEVICE AND SYSTEM FOR INTRACAVITY PROBE PROCEDURE PLANNING

CROSS-REFERENCE TO RELATED APPLICATION(S)

The present application claims priority from U.S. Provisional App. No. 62/774,800, filed on Dec. 3, 2018, herein incorporated by reference in its entirety.

BACKGROUND

1. Field

The present disclosure relates to the field of medical interventions. More particularly, the present disclosure relates to a method for preparing or planning a medical intervention, such as a structural heart procedure.

2. State of the Art

Structural heart disease covers a wide range of cardiac conditions, including valvular heart disease, arrhythmia, and defects in the muscular structure of the heart. The disease may be congenital, as well as acquired. As the western population ages, acquired disease, such as calcific (senile) aortic stenosis and mitral regurgitation has increased in importance. The past two decades have seen a revolution in the treatment of structural heart disease with transcatheter therapies being developed, for instance, for valve repair and replacement, closure of defects such as ASD (atrial septal defects), and isolation of the left atrial appendage to reduce embolic risk in atrial fibrillation. Patients who previously could only undergo high risk surgical procedures or were completely inoperable can now be treated with a transcatheter approach performed in a catheterization laboratory, often with only a one-night stay in the hospital.

When it comes to structural heart disease treatment, computed tomography (CT) plays an important role in pre-operative transcatheter procedure planning. CT provides the physician with accurate three-dimensional information of the heart structure and possible surrounding structures. For instance, in transcatheter valve replacement or repair, CT has an important role in device selection by determining the anatomy and geometric measurements of the for instance the valve annulus as described by Thériault-Lauzier et al, "Computed Tomography for Structural Heart Disease and Interventions", Interventional Cardiology (2015) September; 10(3): 149-154, where it is concluded that sizing of the patient anatomy and visual anatomical assessments are important for using the appropriate device and making the correct treatment decisions.

Transcatheter procedures, for instance transcatheter aortic valve replacement, are performed in a catheterization laboratory in which X-ray is the fundamental imaging modality. A majority of these transcatheter procedure are performed under the guidance of transesophageal echocardiography (TEE). Due to the TEE's high temporal resolution, possibility to assess blood flow and different tissue response as compared to X-ray as used during a transcatheter procedure, TEE is a complementary imaging modality. For instance, TEE is able to assess the valve leaflets as well as the valve leaflet motion during the cardiac cycle.

TEE is a semi-invasive technique which requires the insertion of TEE probe, being a tube of approximately 10 mm in diameter, in the esophagus. TEE is vital for guiding and monitoring the entire process of transcatheter heart valve procedures. For instance for proper placement of a mitral clip, coaxial alignment of the catheter towards the annulus is crucial for valve deployment, alignment of the catheter with anchors to be positioned in the tissue is crucial for devices needing anchors or devices that need to puncture tissue at pre-set location to guarantee treatment efficacy. All these locations are monitored and guided by means of TEE.

To perform TEE accurately, knowledge of the procedure and anatomy is needed for the echocardiographer and (interventional) cardiologist/surgeon pre-procedurally. The recommendation stated by Cahalan et al. in "American Society of Echocardiography and the Society of Cardiovascular Anesthesiologists" (Anesth Analg. 2002 June; 94(6):1384-8), describe basic recommendations on the appropriate use of peri-operative (during the procedure) TEE, with the intent of improving outcomes with evidence-based use of TEE. In addition, within these recommendations the description of 8 additional views on top of the 20 currently used views are described as a response to the newer upcoming transcatheter heart procedures. As described in these recommendations the clinical indication for TEE should be the primary determinant of which views are obtained first as well as the level of detail that is obtained from each view. It furthermore describes that the positioning of the TEE imaging device to obtain certain views is different per patient because of individual variation in the anatomic relationship of the esophagus to the heart. For example, in some patients the esophagus is adjacent to the lateral portion of the atrioventricular groove, whereas in others it is directly posterior to the left atrium. Shiota et al, "Role of echocardiography for catheter-based management of valvular heart disease", Journal of Cardiology 69 (2017) 66-73, also states that it is important to realize that additional images, beyond the described 28 views, may be necessary to comprehensively image specific structures e.g. for transcatheter heart procedures alignment of the catheter with cardiac structure to implant cardiac device. In addition, the degree of rotation of the transducer and additional manipulation such as right or left flexion, anteflexion or retroflexion, and turning of the probe may be required in individual patients to achieve optimal TEE images.

It is well known that the quality of images obtained by TEE, and how they are aligned with the device that is deployed, strongly relies on the experience of the echocardiographer. It is therefore crucial that the echocardiographer holds an accurate knowledge of the anatomy and function of the heart structure and implantable device. Since TEE is a highly user-dependent imaging modality, proper steering of the probe, spatial location, accurate knowledge of the anatomy and function the heart structure and implantable device play a vital role. Furthermore, complications such as small bleedings, chocking, cardiac arrhythmias and esophagus bleeding can occur during TEE imaging.

TEE simulation techniques are available with the aim to improve the skills of the echocardiographers. US patent application 2009/0162820 discloses an education simulator for TEE, which includes a phantom which mimics the human upper body and a predefined heart model. EP 2538398 discloses a method that uses a three-dimensional model based on multiple CT images to simulate a TEE procedure for training TEE operators. Both US2009/0162820 and EP 2538398 are aimed to provide TEE simulation for education purposes.

The vascular anatomy of patients who undergo a transcatheter heart procedure is deviating from normal population and huge deviations between patients are presents. To allow pre-operative planning within the setting of structural heart procedure for TEE imaging, patient specific volumetric image data is required. Further to support in the desired TEE image view, patient specific anatomical landmarks identified within the volumetric image dataset is required.

There is thus a need for a system that enables physicians (e.g. the echocardiographers) to plan TEE imaging for a specific patient. The disclosed method will also predict optimal parameters for obtaining particular standard views (for instance "4 chamber"). Without these predictions, physicians need to search for the optimal orientation during the procedure. The disclose method will thus lead to shorter procedures and reduced patient risk.

SUMMARY

It is thus an object of embodiments herein to provide a method of planning a medical intervention on patient that involves an intracavity probe, such as a TEE or intravascular probe. The method uses an imaging dataset of the patient. The method includes selecting a view-type from a defined set of view-types, determining a virtual field of view of the probe corresponding to the selected view-type, rendering for display a virtual intracavity image based upon the imaging dataset of the patient and the virtual field of view of the probe.

In embodiments, the virtual field of view can be based upon segmentation of an intracavity path of the probe and at least one anatomical structure.

In embodiments, the virtual field of view can be based upon probe parameters computed in accordance with a pre-defined set of rules for the selected view-type. The probe parameters can be computed by evaluation of cost function expressed by the pre-defined set of rules for the selected view-type. The predefined set of rules can vary over the view-types in the set of view-types.

In embodiments, the virtual field of view can be determined from probe parameters, which include a probe location, a view direction and a plane orientation.

The method can further include selectively adjusting probe parameters of the probe, recalculating a virtual field of view of the probe based upon the adjusted probe parameters, and rendering for display another virtual intracavity image based upon the imaging dataset of the patient and the recalculated virtual field of view of the probe.

The method can also further include selectively storing data representing the virtual intracavity image and the corresponding probe parameters as part of a plan.

In embodiments, the imaging dataset of the patient can be acquired using a volumetric imaging modality selected from the group consisting of X-ray CT imaging, rotational angiography, Mill, SPECT, PET, three-dimensional ultrasound, and the like.

In another aspect, a method of medical intervention on patient is provided that involves an intracavity probe, such as a TEE or intravascular probe. The method includes storing data representing at least one virtual intracavity image and corresponding probe parameters of the probe as part of a plan for the medical intervention. With the probe located and oriented to correspond to certain probe parameters stored as part of the plan, a live intracavity image is acquired by operation of the probe. A display is generated that displays together a virtual intracavity image stored as part of the plan and the live intracavity image.

In another aspect, devices, program products and methods are considered that store data representing at least one virtual intracavity image and corresponding probe parameters of the probe as part of a plan for the medical intervention. With the probe located and oriented to correspond to certain probe parameters stored as part of the plan, a live intracavity image is acquired by operation of the probe. A display is generated that displays together a virtual intracavity image stored as part of the plan and the live intracavity image.

Embodiments also relate to a system for planning a medical intervention on patient that involves an intracavity probe, where the system includes memory configured to store an imaging dataset of a patient and at least one processor. When executing program instructions stored in the memory, the at least one processor is configured to execute one or more steps of the method according to embodiments herein. In a specific embodiment the at least one processor is configured to access the imaging dataset of the patient, select a view-type from a defined set of view-types, determine a virtual field of view of the intracavity probe corresponding to the selected view-type, and render for display a virtual intracavity image based upon the imaging dataset of the patient and the virtual field of view of the intracavity probe.

The system may further comprise an imaging acquisition subsystem and an intracavity probe such as a TEE probe or ICE probe. The imaging acquisition subsystem can be configured to acquire images from the intracavity probe.

The system may further comprise a volumetric imaging acquisition subsystem that is configured to acquire the imaging dataset of the patient. The volumetric imaging acquisition subsystem may advantageously use a volumetric imaging modality selected from the group consisting of X-ray CT imaging, rotational angiography, SPECT, PET, three-dimensional ultrasound, and the like.

The imaging acquisition subsystems may be part or may be interfaced to a more general system for medical intervention planning. In an advantageous configuration, it is the imaging acquisition system that comprises medical intervention planning capability, for example including memory and processors, either dedicated or of the general purpose type that are configured to perform the method steps according to embodiments herein. Such imaging acquisition system can equivalently be either the volumetric acquisition system or the intracavity acquisition system depending on the circumstances and the availability of processing devices. This will allow to manufacture a very compact system.

Other aspects and improvements are described and claimed.

BRIEF DESCRIPTION OF THE DRAWINGS

The characteristics of the invention and the advantages derived therefrom will be more apparent from the following description of non-limiting embodiments, illustrated in the annexed drawings.

DETAILED DESCRIPTION OF THE PREFERRED EMBODIMENTS

The present application is particularly advantageous in pre-operated planning of intracavity imaging (such as TEE or intracardiac imaging) during transcatheter heart procedures based on patient specific CT image dataset as acquired with a CT system and it will mainly be disclosed with reference to this field, particularly for planning for structural heart procedures for instance heart valve replacement, valve repair and left atrium appendix (LAA) closures. An intracavity probe is an imaging device, for example of the ultrasound type, that, inserted in a cavity or orifice of the body (such as, for example, the esophagus, the rectum, the vagina, a vessel (artery or vein), heart atrium, heart ventricle, etc.) and provides images therefrom.

Figure 1:
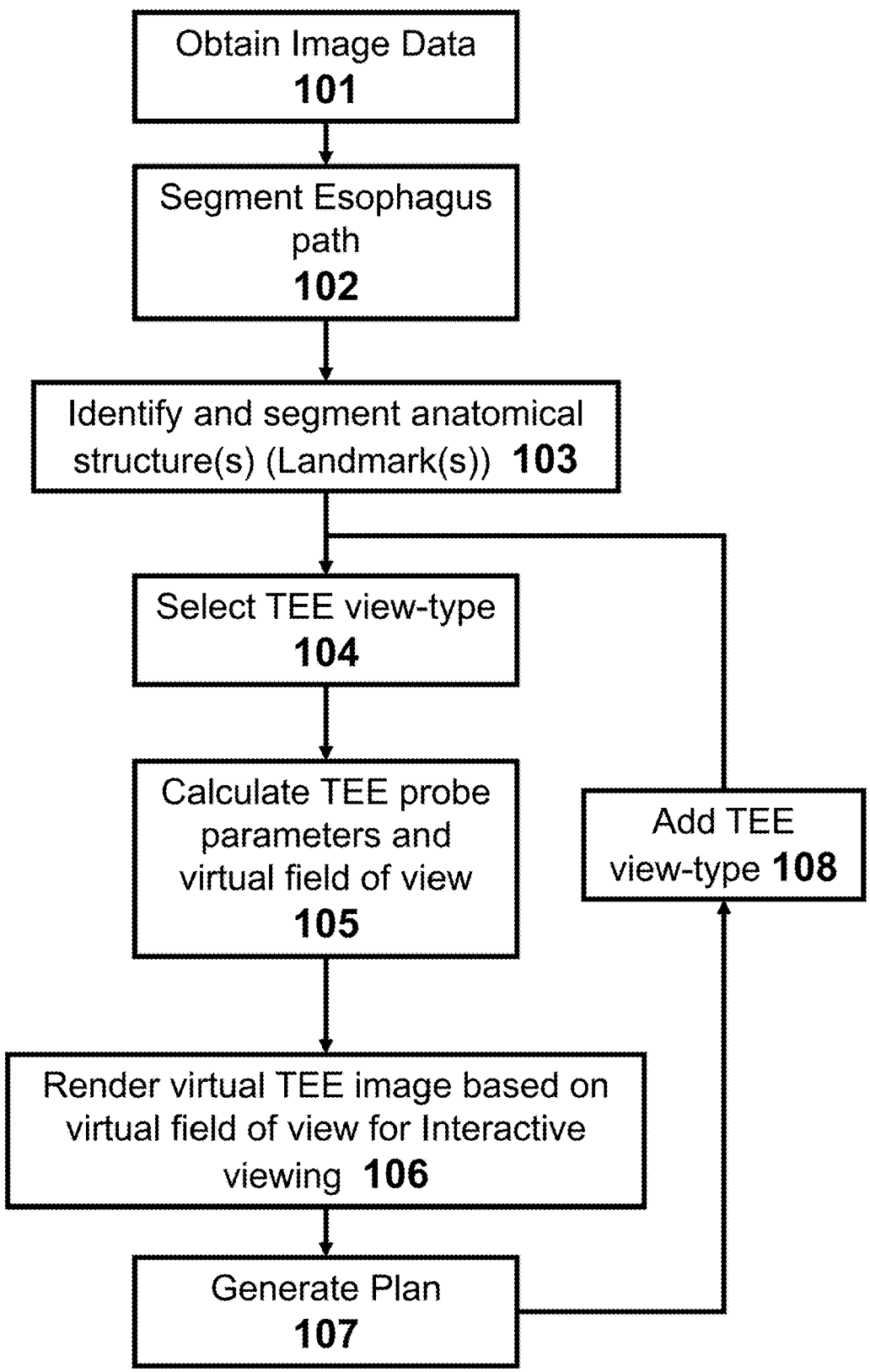
FIG. 1 shows an exemplary flow chart of an embodiment of the present application.

FIG. 1 shows a flow chart illustrating the operations according to an embodiment of the present application. The operations employ an imaging system capable of acquiring and processing volumetric images, for instance computed tomography, of an organ (or portion thereof) or other object of interest.

Figure 2:
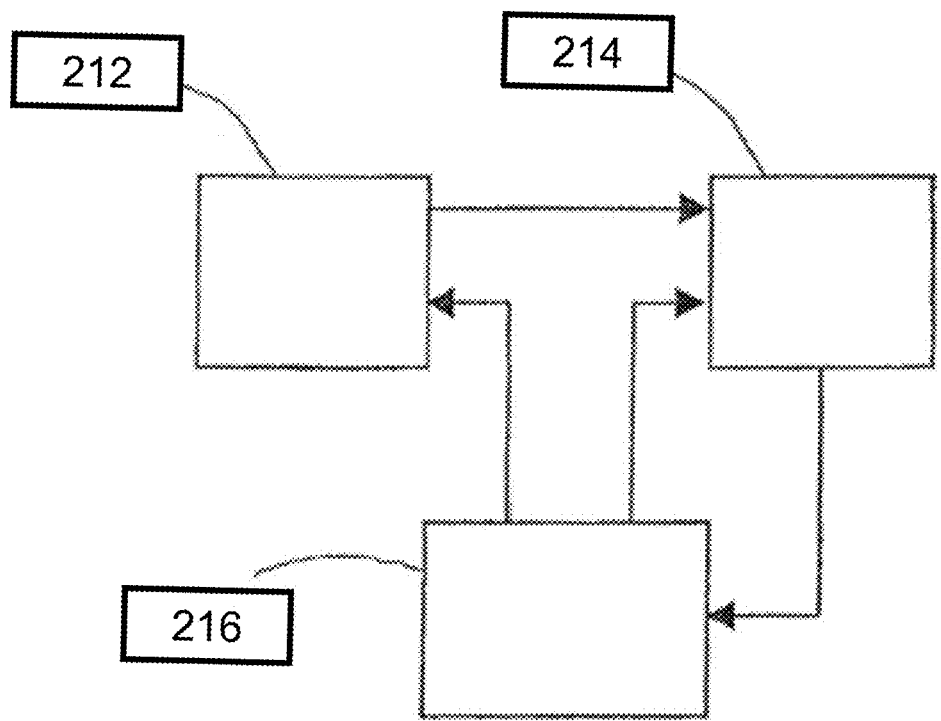
FIG. 2 shows a functional block diagram of an exemplary X-ray CT system.

FIG. 2 is a functional block diagram of an exemplary X-ray CT system, which can be used for the imaging system that is part of the operations of FIG. 1. The exemplary X-ray CT system includes a CT imaging apparatus 212 that operates under commands from user interface module 216 and will provide data to data processing module 214.

The X-ray CT imaging apparatus 212 captures a CT scan of the organ of interest. The X-ray CT imaging apparatus 212 typically includes an X-ray source and detector mounted in a rotatable gantry. The gantry provides for rotating the X-ray source and detector at a continuous speed during the scan around the patient who is supported on a table between the X-ray source and detector.

The data processing module 214 may be realized by a personal computer, workstation or other computer processing system. The data processing module 214 processes the CT scan captured by the X-ray CT imaging apparatus 212 to generate data as described herein.

The user interface module 216 interacts with the user and communicates with the data processing module 214. The user interface module 216 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 214 and the user interface module 216 cooperate to carry out the operations of FIG. 1 as described below.

The operations of FIG. 1 can also be carried out by software code that is embodied in a computer product (for example, an optical disc or other form of persistent memory such as a USB drive or a network server). The software code can be directly loadable into the memory of a data processing system for carrying out the operations of FIG. 1.

An embodiment is now disclosed with reference to FIG. 1. The therein-depicted steps can, obviously, be performed in any meaningful logical sequence and can be omitted in parts. As it is an objective of the embodiments herein to provide a select (e.g. optimal) workflow that can be used for planning the TEE imaging during transcatheter heart procedures based on patient specific CT image dataset, workflow example steps will also be referenced.

As can be seen in FIG. 1, the workflow comprises of number of steps. First patient specific image data is obtained as described in step 101 of FIG. 1. The patient specific image data represents a volumetric image dataset such as for instance obtained with a CT scanner. The patient specific image dataset may also consist of four-dimensional (4D) data, which is a time sequence of three-dimensional (3D) that depict the cardiac motion.

In step 102 of FIG. 1, the path of the esophagus is segmented within the patient specific image dataset. This path represents the 3D centerline of the esophagus. For determining this centerline, similar techniques can be applied as those used for segmenting blood vessels centerlines, being manual delineation, or automatic as for instance disclosed by Grosgeorge et al, "Esophagus Segmentation from 3D CT Data Using Skeleton Prior-Based Graph Cut", Comput Math Methods Med. 2013; 2013: 547897.

In step 103 of FIG. 1 one or more anatomical structures (landmarks) are identified and segmented. By using the volumetric image data, it is possible to label and segment (or delineate) one or more anatomical structures using manual, semi-automatic or fully automatic methods. An example of manual segmentation of a mitral valve is provided by Thériault-Lauzier et al, "Quantitative multi-slice computed tomography assessment of the mitral valvular complex for transcatheter mitral valve interventions part 1: systematic measurement methodology and inter-observer variability", EuroIntervention. 2016 Oct. 10; 12(8): e1011-e1020. An example of (semi) automatic segmentation of the four chambers within the heart is provided by Zhen et al, "Four-Chamber Heart Modeling and Automatic Segmentation for 3D Cardiac CT Volumes Using Marginal Space Learning and Steerable Features", IEEE Trans Med Imaging. 2008 November; 27(11):1668-81. Another example of semi-automatic segmentation of a heart valve employs user-provided seed point(s).

Table 1 provides some examples of anatomical structures (landmarks) with their corresponding structure types that support in the determination of TEE views as performed by step 105 of FIG. 1. Some of the structure types are simple 3D locations (Points), some are closed 3D curves (Closed curve) and some are segmented 3D structures (e.g., tube-like structure).

TABLE 1

Examples of landmarks with their corresponding structure type

| Landmark | Structure Type |
| --- | --- |
| Mitral annulus | Closed curve |
| Tricuspid annulus | Closed curve |
| Aortic annulus | Close curve |
| Pulmonary valve | Tube like structure |
| Fossa Ovalis | Closed curve |
| Apex | Point |
| Lower Mitral Commissure | Point |
| Upper Mitral Commissure | Point |
| Atrial appendage | Tube like structure |
| SVC (Superior Vena Cava) | Tube like structure |
| IVC (Inferior Vena Cava) | Tube like structure |

All of the above anatomical structures can be segmented manually and/or semi-automatically. For the calculation of the TEE probe parameters (step 105), it does not matter if the landmarks are segmented automatically, semi-automatically or manually. For example, the mitral annulus landmark is often manually delineated by placing a collection of user defined points as for instance described by Blanke et al, "Mitral Annular Evaluation with CT in the Context of Transcatheter Mitral Valve Replacement", JACC Cardiovasc Imaging 2015 May; 8(5):612-615. As can be seen from the Table 1, some landmarks are points, some are closed curves, and some are tube like structures.

Figure 3:
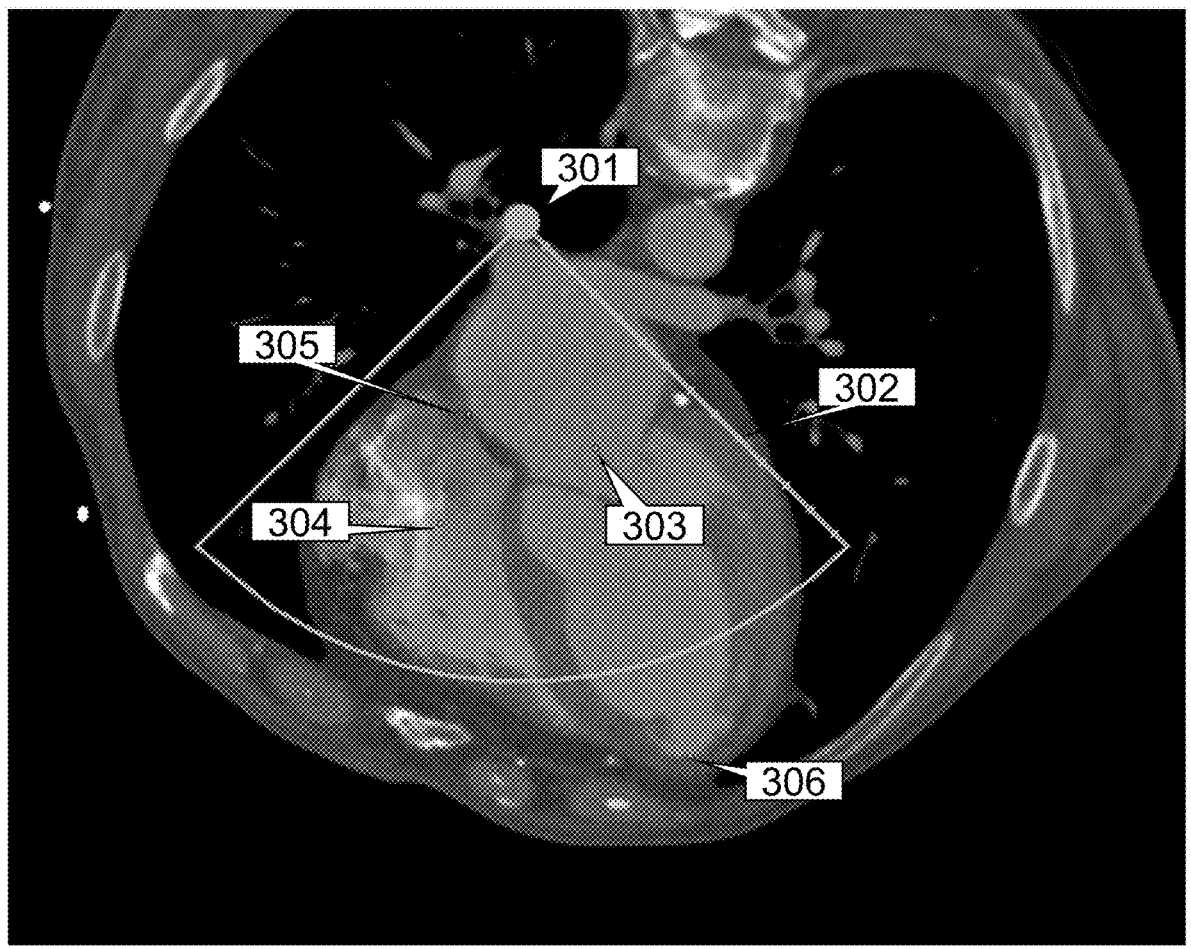
FIG. 3 shows a Multi Plane Reformatting of a four-chamber view.

An example that depicts how these anatomical structures (landmarks) can be used is shown in FIG. 3. FIG. 3 shows a Multi Plane Reformatting (MPR) of a four-chamber view based on the patient specific volumetric image data. This four-chamber view is defined by a 2D image plane which is based on identified landmarks. This image plane is chosen to cut through the center of the mitral valve 303, the tricuspid valve 304 and fossa ovalis 305, as well as the apex of the heart 306. The planned TEE probe location 301 and virtual field of view 302 are superimposed within this MPR view. In this example, some of the target structures are points and closed curves and the image plane intersects with the centers of these structures. The centers of the closed curved structures can be calculated by computing the center of gravity of the 3D closed curved. A second example is provided by FIG. 4.

Figure 4:
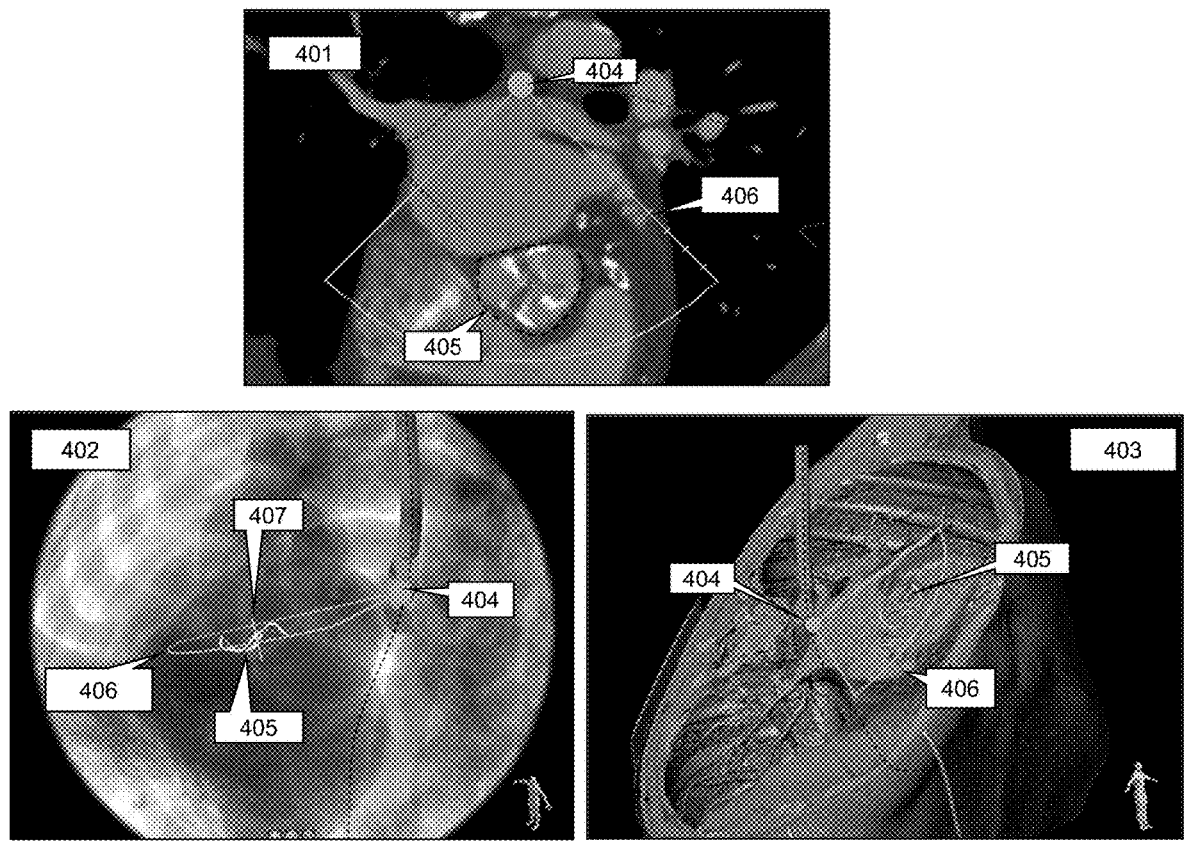
FIG. 4 show an example of a planned TEE within an MPR reconstruction, simulated angio view and a volume render view.

FIG. 4 shows an MPR reconstruction 401, simulated angio view 402 and a volume render view 403. Within all these three views, the TEE probe location 404, closed curve 405 that indicates the aortic valve annulus and the TEE virtual field of view 406 are shown. In this example, the field of view is defined by a plane calculated from the 3D closed curve 405.

If the operator is preparing for an interventional procedure, he/she might place virtual devices (replacement valves, repair devices and or delivery devices) that will be placed or are temporarily present during the procedure. The locations for these devices will be estimated based on the segmentations and the content on the images. An example of such a device is the MitraClip and further described by Feldman et al in "Percutaneous mitral repair with the MitraClip system: safety and midterm durability in the initial EVEREST (Endovascular Valve Edge-to-Edge Repair Study) cohort", J Am Coll Cardiol. 2009 Aug. 18; 54(8): 686-94.

Figure 5:
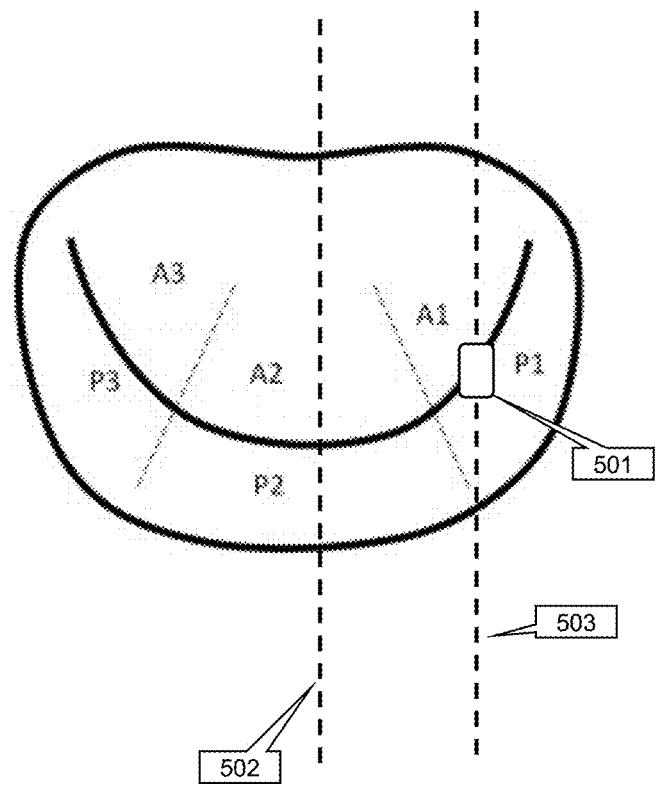
FIG. 5 shows a schematic representation used for planning for placement of a MitraClip.

FIG. 5 shows a schematic representation used for planning for placement of a MitraClip. The image shows the mitral valve, with the location of the MitraClip device 501 the physician wants to place during the procedure. Intersection line 502 shows where the TEE image view normally intersects the mitral valve. During the procedure, this intersection should be at location 503, such that the mitral clip 501 is visible in the TEE image. The locations of these devices can also be used to calculate additional device specific views.

The operator (for instance, the echocardiographer) may decide that it's not beneficial to segment heart structures. This may be necessary in the case that the anatomy cannot be segmented automatically due to image quality or rare anatomic variations. In this case, step 103, 104 and 105 can skipped and the operator can determine the TEE probe parameters and the virtual TEE interactively as described by step 106.

In step 104 of FIG. 1, the operator chooses a TEE view-type he/she intends to plan. For example, a desired TEE view-type can be selected from the following view-types: e.g. two-chamber view-type, four-chamber view-type, bicaval view-type, and mitral commissural view-type.

Figure 6:
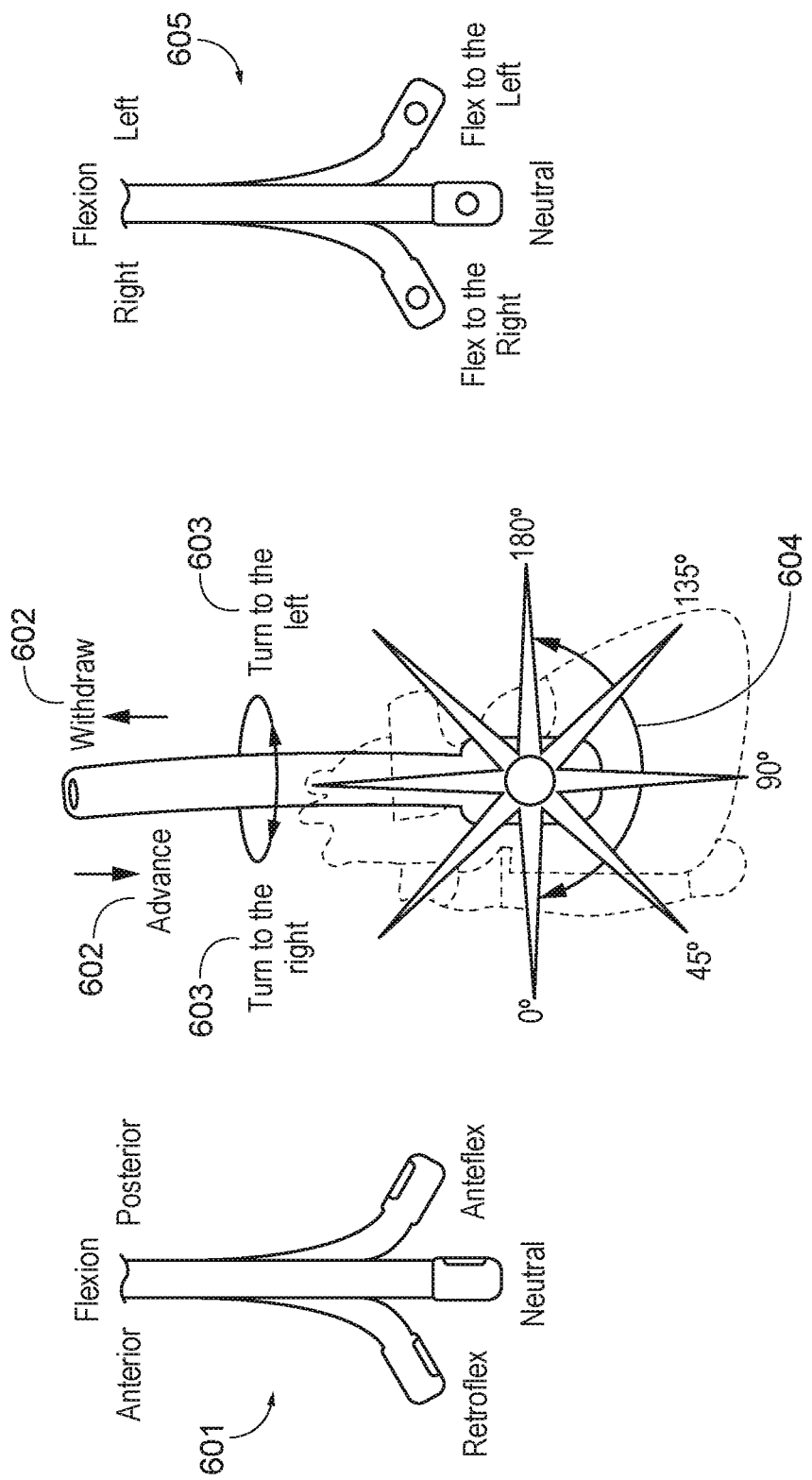
FIG. 6 illustrates the possible movements to manipulate the probe to acquire a TEE image.

In step 105 of FIG. 1, TEE probe parameters for the desired TEE view-type can be calculated as well as the creation of the corresponding virtual TEE view. To determine the TEE probe parameters and the virtual TEE view corresponding to the specific TEE view-type as identified in step 104, five parameters of interest can be computed. FIG. 6 illustrates the five parameters of interest and are explained below:

1. Shaft insertion depth. This parameter defines the depth of the TEE probe inside the esophagus and is archived by advancing or withdrawal (602) of the TEE probe by the echocardiographer. During a TEE scan, the TEE echocardiographer measures the insertion depth from the patient's teeth. As these are rarely included in cardiac image scans such as CT or MM, the operator will have to calibrate against a known height. This calibration step if further described in the workflow depicted by FIG. 13.

The workflow as described by FIG. 1 may allow the operator to set the shaft insertion depth to zero at a particular TEE view simulation (105 and/or 106). All insertion depths are then computed relative to this depth. Such "relative depths" can be used in the workflow as described by FIG. 13 to simplify the depth calibration step 1302.

2. Shaft rotation. This parameter defines the rotation of the shaft along its long axis (603).

3. Transducer rotation angle. This parameter defines the rotation of the TEE transducer (604).

4. Shaft bending anterior-posterior angle. This parameter defines the bending angle of the shaft in anterior-posterior direction (601).

5. Shaft bending left-right angle. This parameter defines the bending angle of the shaft in left-right direction (605).

The system is able to calculate, in the coordinate system of patient specific volumetric image dataset, the virtual field of view that can be achieved by the TEE probe. The TEE probe parameters are computed based upon the segmented esophagus path that result from step 102 of FIG. 1 and the anatomical structures or landmarks (103) which describe the selected TEE view-type (104). For a specific TEE view-type, one or more rules that are associated with one or more anatomical structures are defined for the specific TEE view-type.

Table 2 provides a few examples of TEE view-types and associated rules.

TABLE 2

Examples of view rule database (1003); overview of view rules corresponding to specific TEE view-types.

| View-type Name | View-type rules |
| --- | --- |
| 4 chamber | Probe on Mitral Center-Apex line |
| | Mitral center in middle of FOV |
| | Transducer rotated to show tricuspid valve center |
| BiCaval view | Probe halfway IVC and SVC |
| | Plane intersects IVC center and SVC center |
| | IVC left, SVC right on FOV |
| ME Mitral Commissural | Probe on Mitral Center-Apex line |
| | Mitral center in middle of FOV |
| | Transducer rotated that upper and lower mitral commissures are in plane |
| Mitral Short Axis | Intersects Mitral valve center |
| | FOV approx. in plane with closed curve |
| | Center Mitral valve in Field of view |

Examples of common TEE view-types, as well as orientation recommendations are described by Hahn et al, "Guidelines for performing a comprehensive transesophageal echocardiographic examination: recommendations from the American Society of Echocardiography and the Society of Cardiovascular Anesthesiologists", Anesth Analg. 2014 January; 118(1):21-68.

Figure 7:
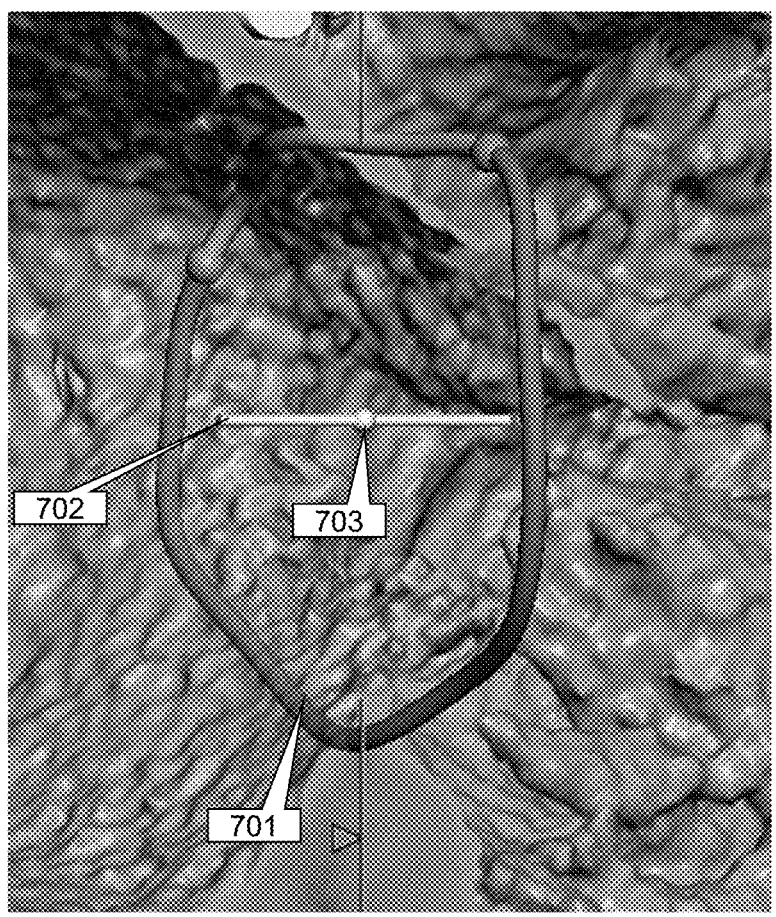
FIG. 7 shows an example of extracting a plane from a closed curved.

Different heart structures (Table 1) and associated rules can be used in different ways when calculating views. In case of a point structure, the rule may require that the point is positioned within the field of view plane, and the rule can specify approximately where this point should appear in the field of view (for example left, middle, right). A closed curve (like the mitral valve), can be simplified to a center point and to a plane which best fits through the closed curve by converting the closed curve to a point cloud and then perform eigenvalue/eigenvector analysis on the point cloud. An example is provided by FIG. 7, which shows a closed curve 701 that indicates the location of the mitral annulus within a volume render view. Line 702 is a line orthogonal to the mitral annulus representing the normal vector of the plane, and landmark 703 the center. Line 702 and landmark 703 implicitly define the annulus plane (with landmark 703 as the origin).

Rules like "Mitral Short Axis" can require the center point of the mitral annulus contour to be positioned within the image plane, centered, and the field of view plane to be aligned with the plane fitted (using for example least squares) through the data points. A 3D tube-like structure can be similarly converted to a center-plane combination by calculating a center(lumen)line through the tube-like structure and using the average position and direction of the centerline. The direction is used as the plane normal. A center lumen line can be calculated for instance using skeletonization of the tube-like structure.

In embodiments, the transducer position and orientation of the TEE probe and the corresponding TEE Field of View of the TEE probe can be calculated by following the esophagus path for the length of the insertion depth, and applying the rotations and bends of the TEE probe.

Figure 8:
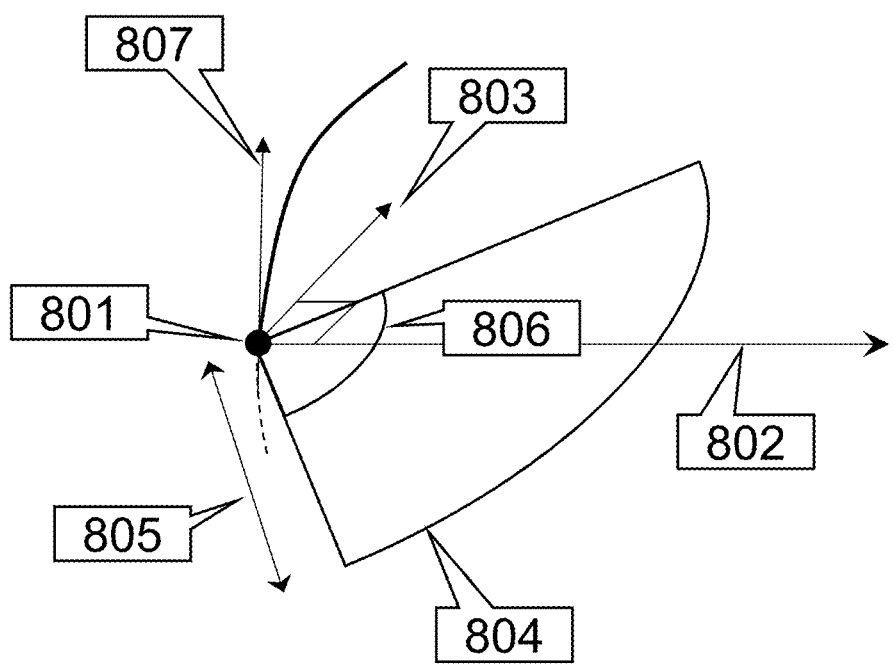
FIG. 8 shows a schematic representation of the virtual field of view.

For example, let H be a 3×3 matrix that represents the transducer orientation system of the TEE probe, consisting of three vectors X (803), Y (802), Z (807) pointing left, forward, and up, relative to the transducer of the TEE probe as can be seen in FIG. 8. The position L (801) represents the location of the transducer of the TEE probe. The Field of View plane (804) of the TEE probe can be identified by the position L (801) and X (803), Y (802) vectors representing, respectively, the view direction and plane orientation.

First, the transducer orientation/location $H_d$, $L_d$ can be determined after inserting the shaft of the TEE probe down the esophagus over a distance d (602), and applying the shaft rotation ζ (603). The esophagus path is expressed as a list of points E connected by line segments. The initial transducer location $L_0$ is the start of the esophagus, $E_0$. L is translated along each line segment of E until a total distance d is traveled along the path. $H_0$'s Z axis is aligned with the first line segment of E.

For all the points on E traversed, coordinate system H is multiplied by a rotation matrix:

$$H_k = R(\arccos(n_k \cdot n_{k-1}), n_k \times n_{k-1}) \cdot H_{k-1} \qquad \text{Eqn. (1)}$$

Here, vector $n_k$ is the normalized direction of line segment k, $R(\alpha, v)$ is a function that produces a rotation matrix that rotates over angle α around vector v.

Next, the shaft rotation ζ of the TEE probe is applied to the transducer orientation $H_k$ (the orientation after passing the last point of E traversed) as follows:

$$H_d = R(\zeta, Z_k) \cdot H_k \qquad \text{Eqn. (2)}$$

Next, the anterior/posterior flex angle (φ, 601), the left/right flex angle (θ, 605) and the transducer angle α (604) are applied. Because of the catheter design, φ and θ both affect the probe location and orientation. The location $L_{flex}$ and the orientation $H_{flex}$ of the TEE probe can be calculated as:

$$L_{flex} = L_d + c \cdot \sin\varphi \cdot Y_d + c \cdot \sin\theta \cdot X_d + c \cdot (1 - \cos\varphi \cdot \cos\theta) \cdot Z_d \qquad \text{Eqn. (3a)}$$

$$H_{flex} = R(\theta + \alpha, Y_d) \cdot R(\varphi, X_d) H_d \qquad \text{Eqn. (3b)}$$

Note that constant c is a probe constant representing the bending length.

The parameter $L_{flex}$ represents the location position L (801) of the TEE probe as shown in FIG. 8. The parameter $H_{flex}$ represents the transducer orientation system H of the TEE probe, consisting of three vectors X (803), Y (802), Z (807) as shown in FIG. 8. As can be seen in FIG. 8, the Field of View plane (804) of the TEE probe can be identified by the solved for L (801), X (803), Y (802) vectors. Note that the transducer orientation system is based on the transducer rotation angle α, which can be performed by physical rotation or electronically, but this makes no difference as to the calculation of the location and orientation of the TEE probe transducer. Finally it must be noted that the calculations here are good approximations. However, in alternate embodiments, the calculations for location and orientation of the TEE probe transducer and corresponding field of view can possibly account for tissue stiffness and/or probe physical properties and/or other factors.

Figure 9:
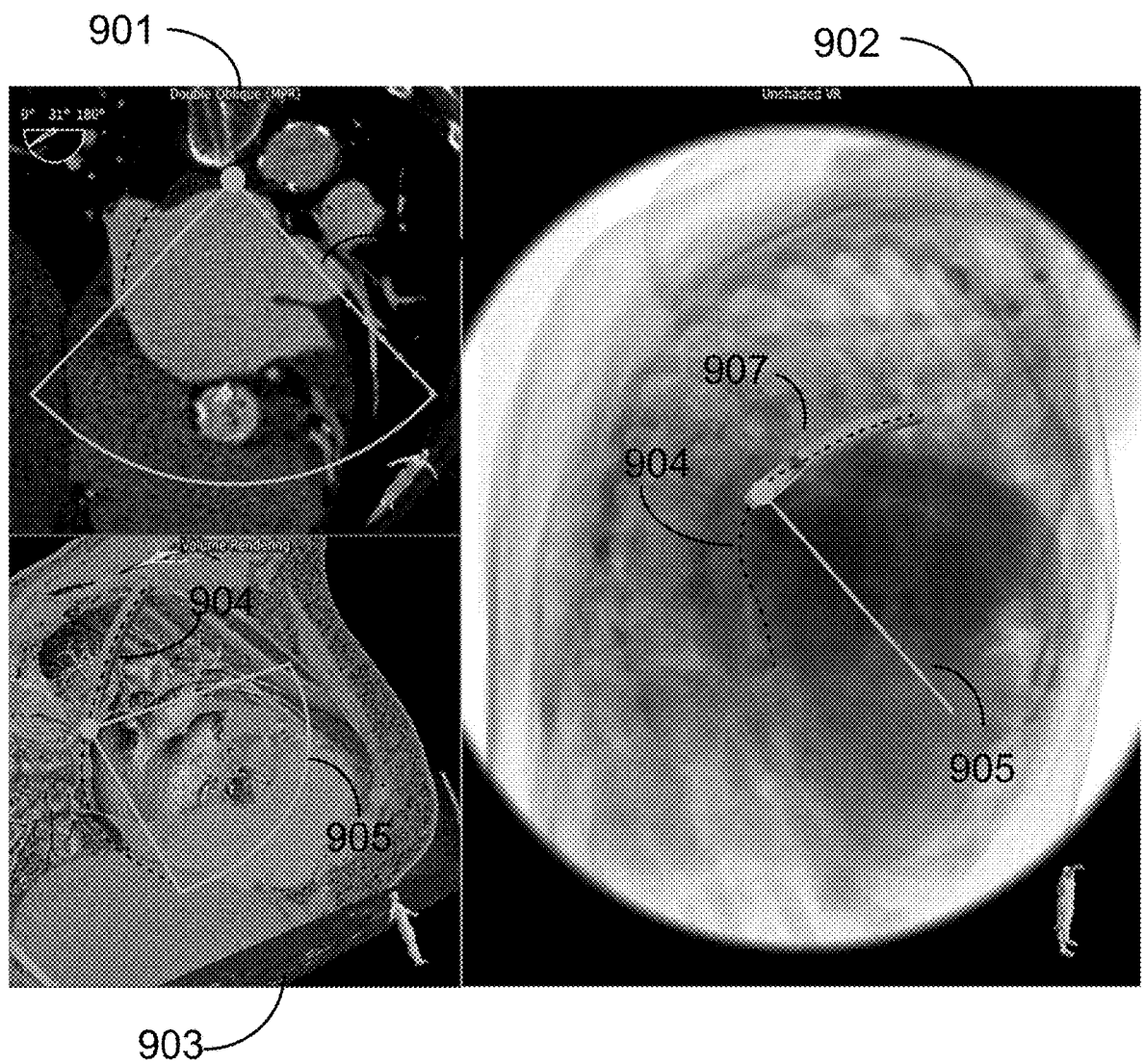
FIG. 9 shows a screen layout of the planned TEE view.

FIG. 9 shows a possible screen layout. The images are rendered using date from dataset 101, in this case CT data. Viewport 901 shows a view that simulates the TEE field of view 905. It mimics the layout of a TEE console, including the indicator 906 of the transducer angle 604. Viewport 902 shows a simulated angio view with the esophagus path 904, probe 907 and field of view 905 indicated. Viewport 903 shows a volume rendering where part of the patient is made opaque, and the esophagus path 904, and field of view 905 are indicated.

If flexing (601, 605) is employed, the probe origin can move away from the original esophagus path. In the patient, the probe does not actually leave the esophagus, instead, the esophagus is deformed. For the above calculations it is assumed that the esophagus deforms with no resistance.

Figure 10:
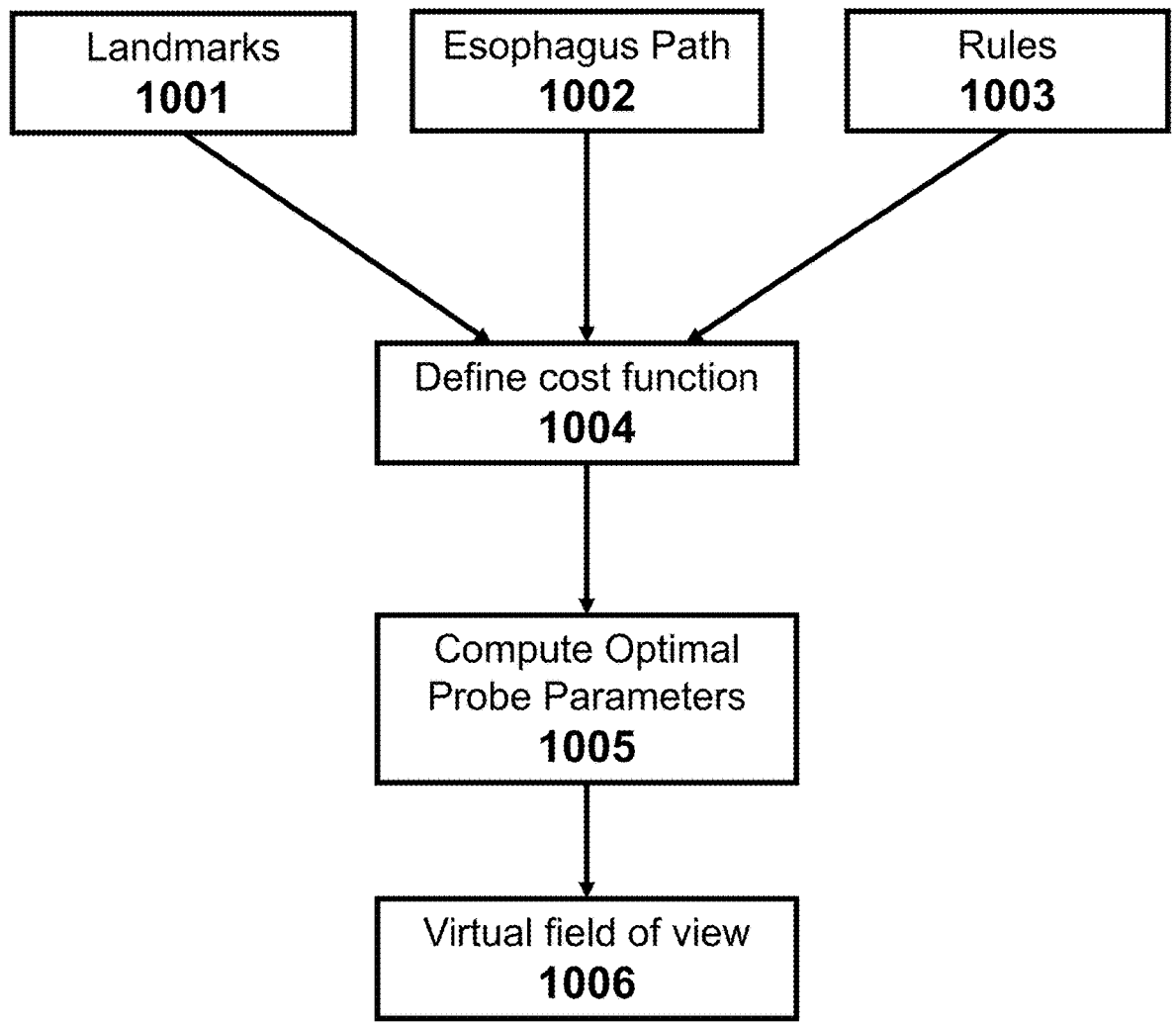
FIG. 10 shows an exemplary flow chart for computing the TEE probe parameters and the virtual field of view.

FIG. 10 describes in detail the method to compute the TEE probe parameters and the virtual field of view of the TEE probe based upon the anatomical structures or landmarks (1001) that result from step 103 of FIG. 1, the esophagus path segments (1002) that result from step 102 of FIG. 1 and the TEE view rules database (1003) which describe the selected TEE view-type as defined by step 104 of FIG. 1.

In step 1004 of FIG. 10, a cost function is defined. For instance, if the virtual field of view of the TEE probe should intersect with a specific landmark, the cost function contribution will be the lowest if it is an exact intersection and the cost increases with larger distance from that specific landmark. For a desired TEE view-type as defined by step 104 of FIG. 1, the applicable view rule set is chosen from the view rules database 1003, expressed as a cost function. Using the segmented esophagus path 1002 and the actual landmarks locations 1001, a cost function can be defined for a specific view/patient combination $C_{view}$ (1004) that depends only on the set of probe parameters P. For example, consider an example for a set of parameters P and a TEE Field of View (FoV) calculated from the set of parameters P. If there are two landmarks $L_1$, $L_2$ that should be intersected by the TEE probe and centered in the FoV, a cost function can be defined as follows:

$$\text{Cost}_{total} = W_1 * \text{distance}^2(L_1, \text{plane}_{FoV}) + W_2 * \text{distance}^2(L_2, \text{plane}_{FoV}) + W_3 * \text{distance}^2(C_{L1\ L2}, C_{FoV}),$$ Eqn. (4)

where $C_{L1\ L2}$ is the desired center of the view determined from the midpoint between $L_1$ and $L_2$), $C_{FoV}$ is the current center of the Field of View (FoV), distance$^2$(a, b) is the square of the distance between two points, or between a point and a plane, and $W_1$, $W_2$, $W_3$ are weight factors that indicate weighing for the corresponding terms.

Note that $W_1$ and $W_2$ can be identical to one another, and $W_3$ can be significantly smaller than $W_1$ and $W_2$. These constraints can be useful to get the landmarks $L_1$ and $L_2$ into the plane than it is to have the image centered correctly.

In step 1005 the optimal probe parameters are computed. For some combination of probe parameters $P_{optimal}$ it provides the best match with the view rules, which is when the cost function $C_{view}$ has a minimal cost. This minimum can be searched for with a solver algorithm. Examples of such algorithms are gradient descent algorithm as described by Wright in "Coordinate descent algorithms", Mathematical programming, June 2015, Volume 151, or genetic algorithms, or brute force. For the gradient descent algorithm, the processing starts with an initial set of probe parameters P and then calculates the derivative of the cost function with respect to all parameter values. The derivative of the cost function provides an indication of the direction ΔP that will decrease the cost function the fastest. The set parameters P are updated by adding ΔP and the process is repeated until the cost function is minimized such that is satisfies a stopping criterion.

The database of view rules 1003 may also contain a formula for calculating an initial probe parameter set as input for the cost function $C_{view}$. It is also possible for the user to add constraints (fixed insertion distance, reduced range of flexing) as part of the view rules. Instead of using an algorithm it is also possible to calculate probe parameters by writing a computer program that determines probe parameters analytically or heuristically, using landmarks 1001 and view rules 1003. In such a program the likely first step would be to calculate the desired intersection plane for the field of view and find the intersection with the line describing the esophagus path (1002).

Within step 1006, the virtual field of view of the TEE probe is computed. The field of view is defined as indicated in FIG. 8. The field of view imaging plane (804) is defined by the probe location 801, view direction 802 and the plane orientation 803, calculated from the set of probe parameters $P_{optimal}$.

As depicted in FIG. 8, the virtual field of view (804) of the TEE probe is defined by the view depth (805) and view angle width (806), which describes the wedge shape of a TEE scan. Note that during acquisition of real TEE image by operation of the TEE probe, these parameters can be electronically controlled from the TEE console and determine the tissue area to be imaged. Increasing this area reduces the frame rate and/or TEE image quality. During the calculation of the virtual field of view of the TEE probe, these parameters can be predefined, controlled by the operator, or automatically computed by using the landmarks (1001) and the esophagus path (1002). An example of automatically computing the view depth (805) and view angle width (806) parameters is to include these in the parameter set P. The algorithm can thereby suggest one or more field of views that show the required anatomical landmarks using the smallest possible depth (805) and smallest possible view angle width (806), which improves the image quality of the acquired real TEE image as described within the workflow with reference to FIG. 13. Alternatively, the automatic computation of the view depth (805) and view angle width (806) can take into consideration a predefined width or depth as defined by the operator. For instance, the operator may define that the depth or width has a minimum or maximum value.

Once the virtual field of view of the TEE probe has been computed, the operator can be allowed to interactively view a virtual TEE image corresponding to the virtual field of view in step 106. The operator can possibly adjust the probe parameters, if necessary. The workflow can then recalculate the virtual field of view of the TEE probe based upon the adjusted probe parameters as described above with respect to step 105 and render another virtual TEE image corresponding to the recalculated virtual field of view as part of step 106. Such probe parameter adjustment, field of view re-calculation and rendering can be repeated for multiple iterations, if need be.

Figure 11:
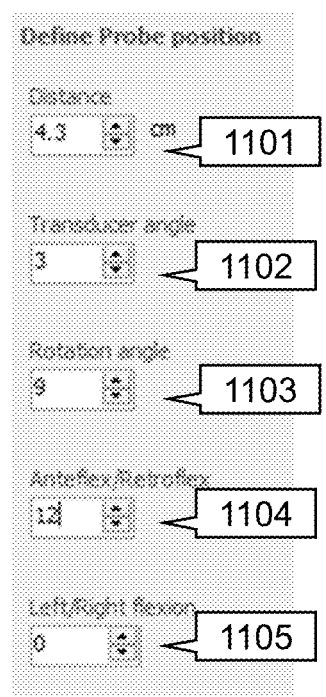
FIG. 11 shows an example user interface with controls to adjust the probe parameters.

FIG. 11 shows an example user interface that allows a user to interactively view a virtual TEE image corresponding to the virtual field of view of the TEE probe as well as adjust the TEE probe parameters, if necessary. The controls shown are insertion distance 1101, transducer angle 1102, shaft rotation angle 1103, ante-retroflex angle 1104 and left-right angle 1105. After changing the values, the virtual field of view 905 of the TEE probe is updated and the renderings in FIG. 9 are updated immediately.

The visualization of the virtual TEE image corresponding to the virtual field of view can be accomplished by rendering the virtual field of view 905 of the TEE probe based on the image data in the volumetric dataset 103. The transducer rotation angle 906 is shown in graphic 901. It is possible to render more realistic virtual TEE images using a color lookup table. In embodiments, the operations can process the cubic volume of voxels of the volumetric dataset to identify an arbitrary plane that cuts through this volume and corresponds to the virtual field of view of the TEE probe, and then interpolate the values for pixels on a virtual image on this plane using the image data for the voxels. This technique is known as MPR or "multi-planar reformatting."

The resulting image will have intensities that match image data for the voxels. A lookup table can be applied to the pixels of the resulting image to transform the intensities in order highlight soft tissue (muscle, fast) and make the remainder black. The lookup table operation can be represented as follows:

$$I = T[\text{val}], \quad \text{Eqn. (5)}$$

where I is the pixel intensity varying from 0.0 to 1.0, corresponding to black and bright white;
T is the lookup table; and
val is the input value of the pixel for the image derived from the multi-planar reformatting Note that the input value for the pixel can be negative. In one example, the lookup table can contain a linear gradient from 1 to 0 for pixel input values in the range −255 to 195, and is 0.0 for other pixel input values.

Figure 14:
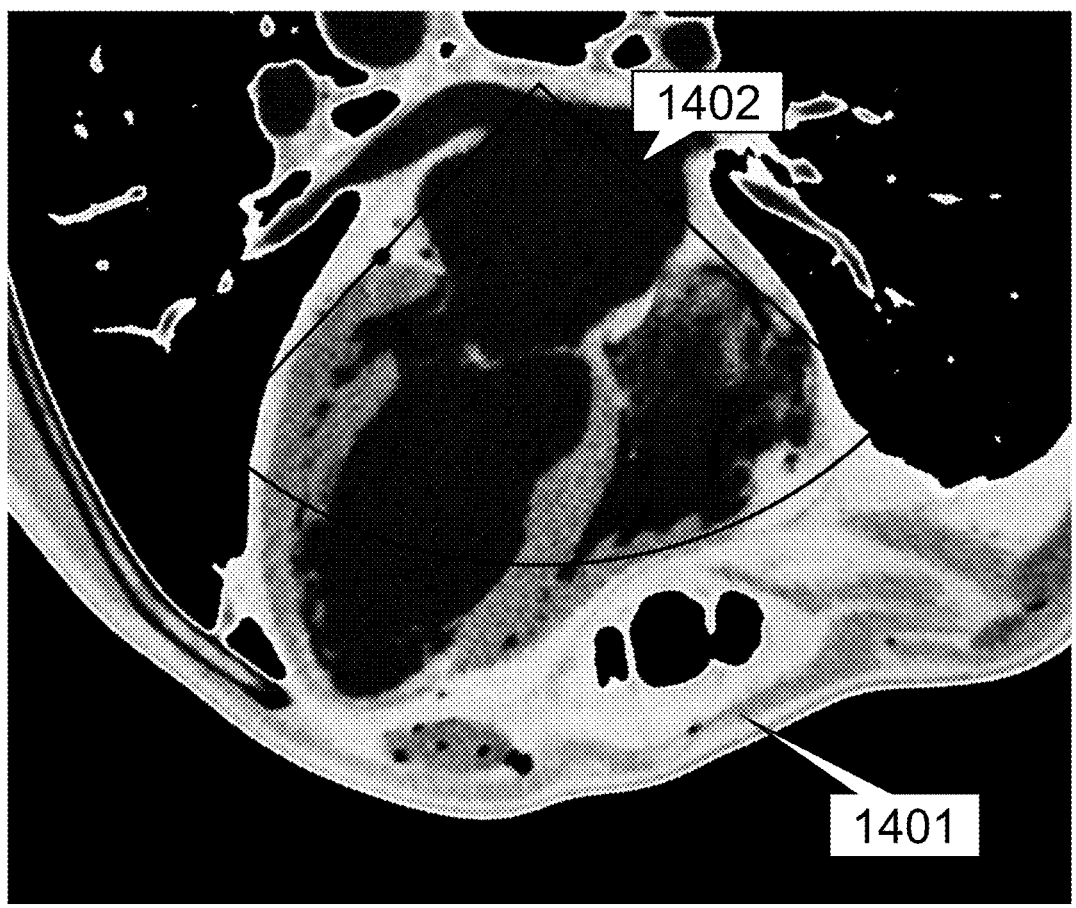
FIG. 14 shows an example of a mimic TEE image based on volumetric image data.

FIG. 14 shows an example of a virtual TEE image (MPR image 1401) based on the image data (101), which is rendered using a color lookup table. The TEE field of view (1402) is superimposed on the virtual TEE image for reference. Lastly, the virtual devices as indicated in step 103 can also be rendered/simulated on the virtual TEE image.

The rendering can be static or use 4D CT data to show how the virtual TEE image at this location will vary due to the movement of the heart. For navigational purposes, the segmented heart structures from the previous step can be superimposed on the virtual TEE images. In addition, the intersection generated can be superimposed on an MPR or volume render 904. There are various techniques for this: intersection lines, embedded planes in volume render, fusing the generated TEE image with the 3D volume render, partial transparency, etc. In addition, an X-Ray angio simulation view (simulated angio view) 902 is shown, that gives a preview of the probe as it will appear on the angio view.

When the operator is satisfied, he/she can generate a planning report or plan as described by step 107 of FIG. 1. This step can involve recording or storing a TEE view as part of the planning report. The TEE view can include the current virtual TEE image and possibly the probe parameters used to generate the current virtual TEE image. Furthermore, the operator can proceed to the next desired view-type (step 108 of FIG. 1) or save the planning report for later use.

The planning report can be used pre-procedurally or during the actual procedure (intra-procedural). Pre-procedurally the report provides visual information whether an intra-procedural real TEE image can be obtained anatomically and can give an estimate of expected TEE image quality obtained during the actual procedure. For instance, for some transcatheter mitral valve procedures the septum between the left and right atrium needs to be punctured by a catheter to get access to the mitral valve. This step in the transcatheter procedure is guided by means of TEE. A virtual TEE image that provides guidance for this puncture is a virtual TEE image that contains both the mitral valve as well as the point where the septum is punctured to obtain access towards the mitral valve. This virtual TEE image can be used to verify the distance between the septal puncture point and the mitral valve. In patients with an enlarged atrium this view is often unobtainable by TEE. Having this information upfront to the actual procedure will therefore provide valuable input for the physician to decide for an optimal treatment.

Another example for use of the report pre-procedurally is to assess intra-procedural TEE image quality. For good quality TEE images, the TEE probe needs to be as close to the tissue of interest. The report will determine the depth of the field of view and will give visual feedback whether other tissues/cardiac structures are located in front of the tissue of interest. If the tissue of interest can only be obtained with a large depth or if other structure(s) is(are) located in front of the tissue of interest, the image quality will be decreased.

During the actual TEE procedure, the operator can use the virtual TEE images and try to obtain real TEE images in the patient that replicate one or more virtual TEE images. An embodiment for this workflow is now disclosed with reference to FIG. 13. During the TEE procedure, the operator opens the TEE plan (1301) as generated within the workflow depicted by FIG. 1, either on paper, or as an electronic document. Next, the operator calibrates the calculated distance offsets (1302) between the TEE plan and the actual patient. The depth/distance values 602 recorded during planning are calibrated against the scale printed on the shaft by manually registering a live TEE image with an image from planning, thus determining the offset between the two scales.

Figure 15:
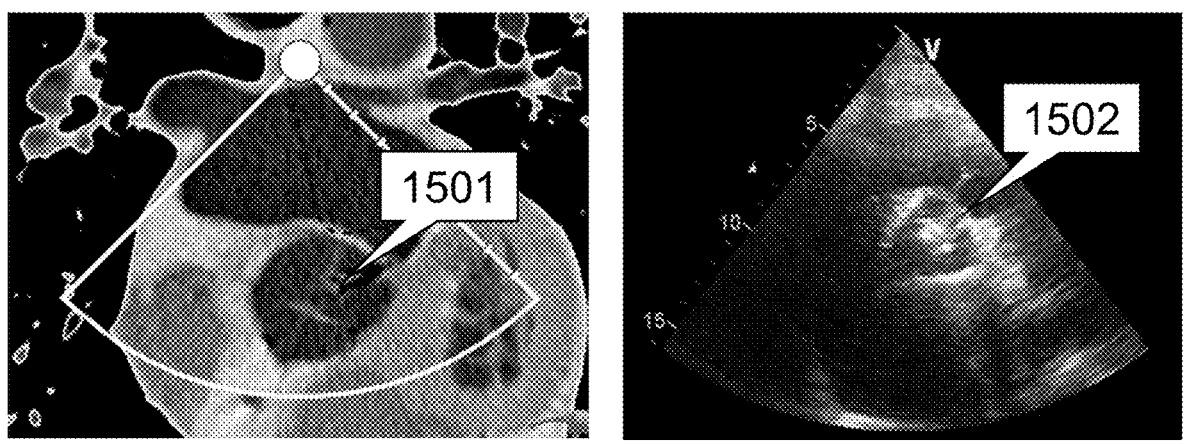
FIG. 15 shows an example for manual matching the planned TEE view with an acquired TEE view using the aortic valve.

One example of such manual matching is by using one of the planned TEE views from the workflow as described by FIG. 1 as a reference TEE view. For all other planned TEE views within the workflow as described by FIG. 1, the computed shaft insertion depth is relative to this reference TEE view. Such reference TEE view can be defined by one or more anatomical structures which is relatively easy to image, for instance the aortic valve. Such manual matching using the aortic valve is illustrated in FIG. 15. The left image shows the aortic valve (1501) on the reference TEE view and on the right the aortic valve (1502) on the live TEE image. If "relative distances" (probe location in the esophagus) is used during the workflow as illustrated by FIG. 1, calibration and re-calibration is done simply reproducing the "zero distance" view on the live TEE image acquired by the TEE probe. To simplify this manual matching process, optionally the reference TEE view can be planned with all probe angle parameters set to 0, and the live TEE image of the probe can be acquired without any rotation as well.

In step 1303, the operator selects a TEE view from the TEE plan and the probe parameters corresponding to the selected TEE view are extracted from the TEE plan.

In step 1304, the operator navigates the TEE probe to the location of the selected TEE view using the probe parameters belonging to the selected TEE view and extracted from the TEE plan in step 1303, and acquires the live TEE image at such location. This process may be repeated (1305) as, until the planned part of TEE review is completed (1306).

Figure 13:
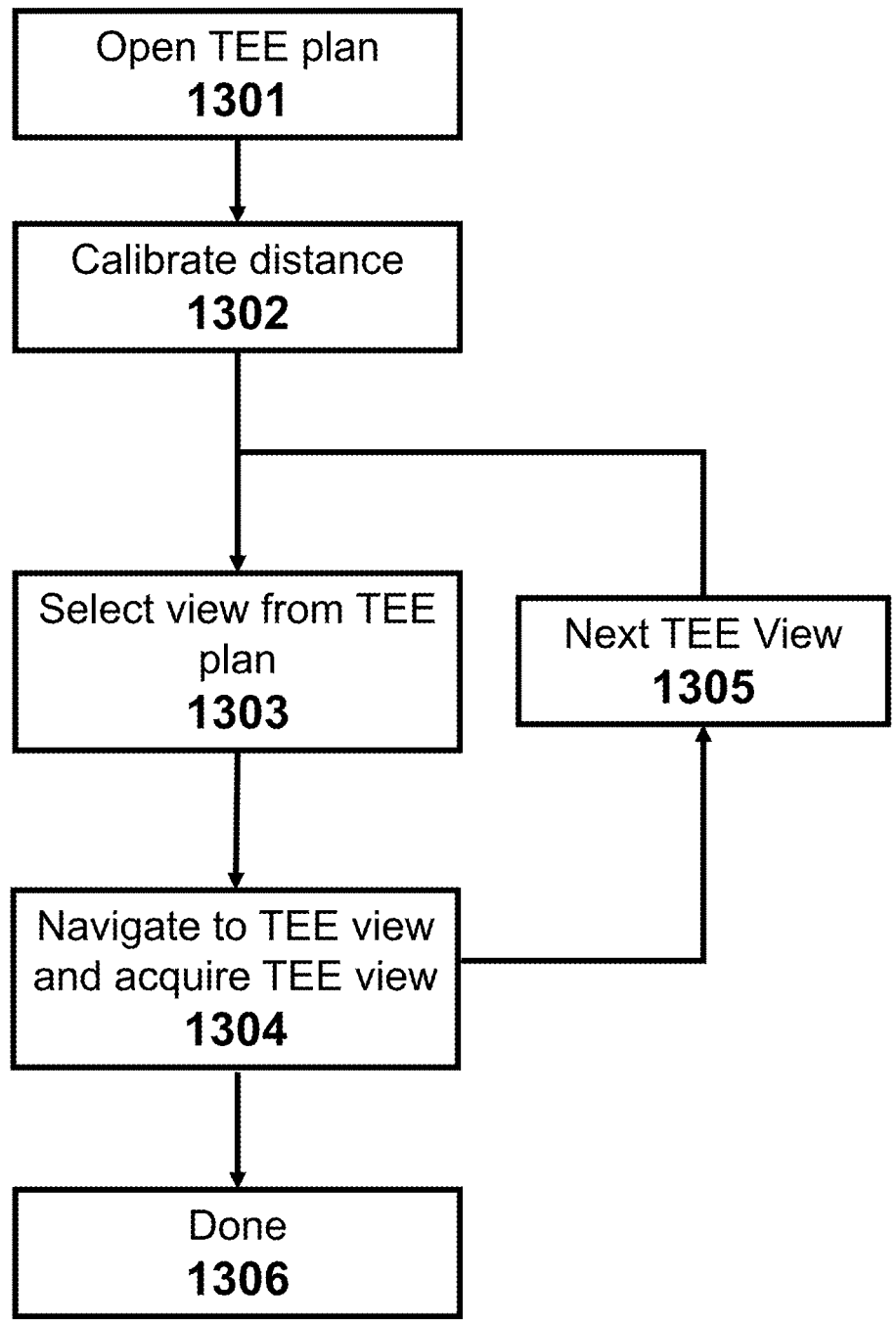
FIG. 13 shows an exemplary flow chart for acquiring a TEE image based on the TEE plan.
Figure 16:
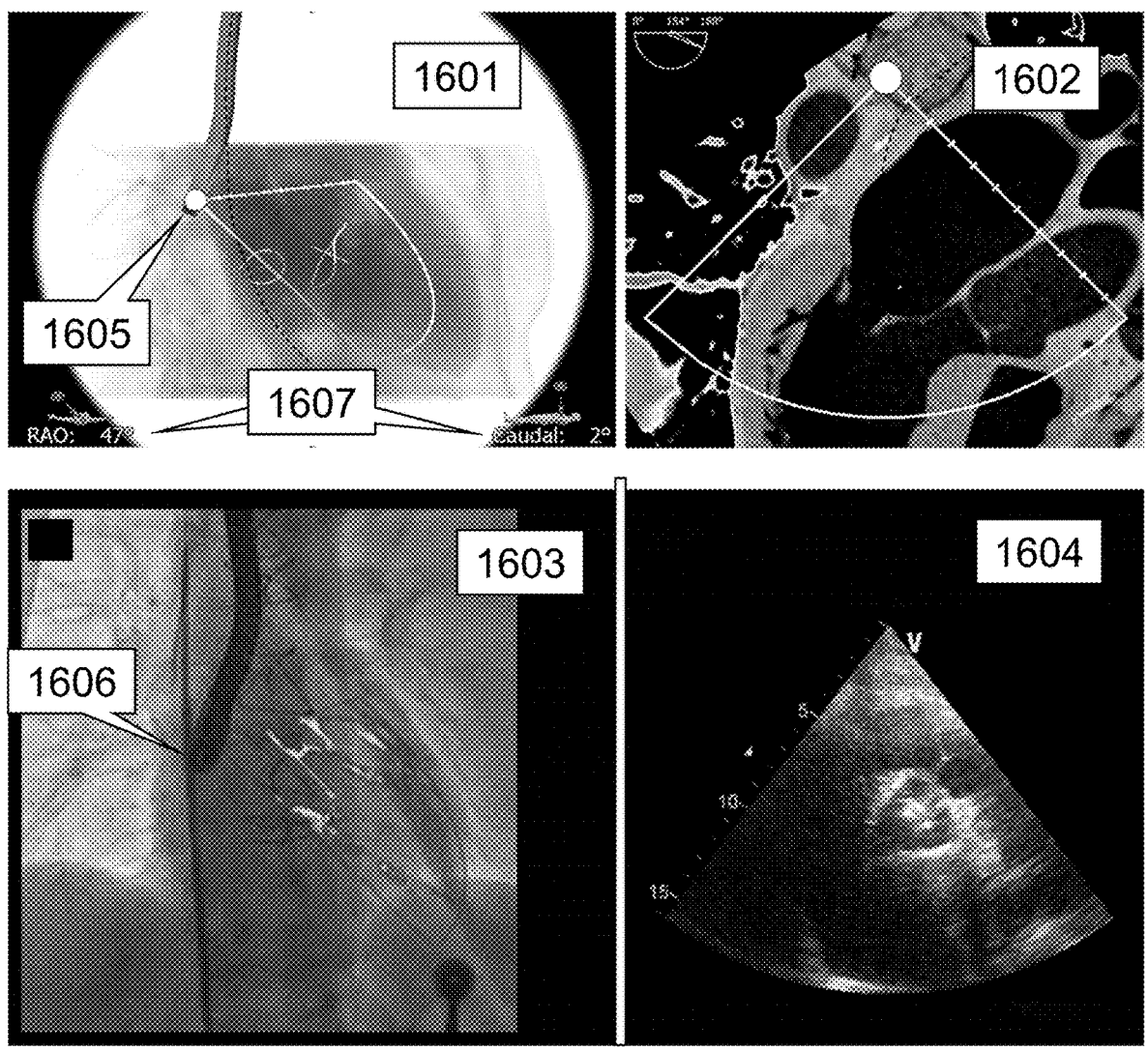
FIG. 16 shows an extended method for registering the planned TEE view with an acquired TEE.

FIG. 16 shows an alternative and extended registration workflow that can be used as part of workflow of FIG. 13. Such registration workflow displays a number of images together, including a simulated angio view (1601) (similar to 902), a virtual TEE view (1602) for one of the planned TEE views, a live procedural X-ray image (1603), and a live TEE view (1604) acquired by the TEE probe that is positioned at the location and orientation corresponding to the virtual TEE view (1602). Registration of the virtual TEE view (1602) and live TEE image (1604) can be performed by matching the probe position (1605) of the simulated angio view (1601) with the probe position (1606) on the live X-ray image (1603). During the workflow as described by FIG. 1, the simulated angio view (1601) calculates the RAO/LAO, caudal/cranial angles (1607) for an optimal or defined c-arm positioning as for instance disclosed by U.S. Pat. No. 9,008,386B2. Alternatively, the steps 105 and/or 106 from FIG. 1 can be performed during the procedure. In this case the simulated angio view (1601) can be computed by the angulation as defined by the X-ray system (RAO/LAO, caudal/cranial angles). In this case the angulation angles (1607) will match the angulation angle of the X-ray image.

Note that if there is minimal mismatch or difference between one or more of the virtual TEE views (1602) of the TEE plan and the corresponding live TEE view (1604), the TEE operator can continue acquiring the live TEE images corresponding to the TEE plan. However, if there is significant mismatch or difference between one or more of the virtual TEE views (1602) of the TEE plan and the corresponding live TEE view (1604), the TEE operator can abandon the TEE plan and fall back on exploratory searching for the best positions for the TEE probe.

Some TEE equipment can capture biplane images, where the biplane image FOV is orthogonal to the original FOV. Such biplane image capture planning can be included in the workflow as described before.

Note that the shaft of the TEE probe can also be freely rotated, but does not require calibration. Specifically, the probe can always be inserted into the patient such that the sensor is pointing to the patient's anterior from the esophagus. If it has been rotated this can be assessed from the orientation of the probe handle.

The workflow described in FIG. 13 uses a plan as input as described within the workflow depicted by FIG. 1. As stated before, this plan can be an (electronic) document, but it could also be machine readable data input for a 3D viewer similar to the software used in the workflow described in FIG. 1.

In addition to the workflow described before, a different embodiment of this invention can exist, in which the workflow depicted in FIG. 1, whether or not combined with the workflow in FIG. 13, can be executed during the actual TEE procedure. In this case it is not required to record the plan as described by step 107 of FIG. 1, but the operator can directly apply the predicted probe parameters.

TEE is a well-established imaging technique to provide exceptionally high resolution images, particularly of the left atrial morphology, the mitral and the aortic valve as well as other important cardiac structures. However, TEE is a moderately invasive procedure that incurs additional risk, cost, and patient discomfort and its application is impeded during interventional procedures because of patient's supine position.

Intracardiac echocardiography (ICE) provides high-imaging resolution and is routinely used during atrial fibrillation (AF) ablation procedures for transseptal puncture and peri procedural catheter visualization. Recently, the use of ICE to guide structural heart procedures is growing (M. Alkhouli et al, "*Intracardiac Echocardiography in Structural Heart Disease Interventions*", JACC: Cardiovascular Interventions, volume 11, issue 21, November 2018).

In contrast to TEE, in which the TEE probe is inserted in the patients esophagus, during ICE the probe is inserted inside of the patients heart through a vein of the patients groin (e.g. femoral vein), arm (e.g. cephalic vein), or neck (axillary vein).

The presently disclosed methods also hold for ICE, with the exception that for ICE the vein needs to be segmented to guide the ICE probe toward the heart instead of the esophagus. For instance, in the case that the ICE probe is inserted through the femoral vein towards the right atrium of the heart, the ICE probe path can extend along the femoral vein, the inferior vena cava vein and the right atrium. This means that within FIG. 1 step 102 becomes "segment vein path". This path represents the 3D centerline of the vein used to guide the ICE probe toward the heart. For determining this centerline, similar techniques can be applied as those discussed at step 102 of FIG. 1 before.

Figure 18:
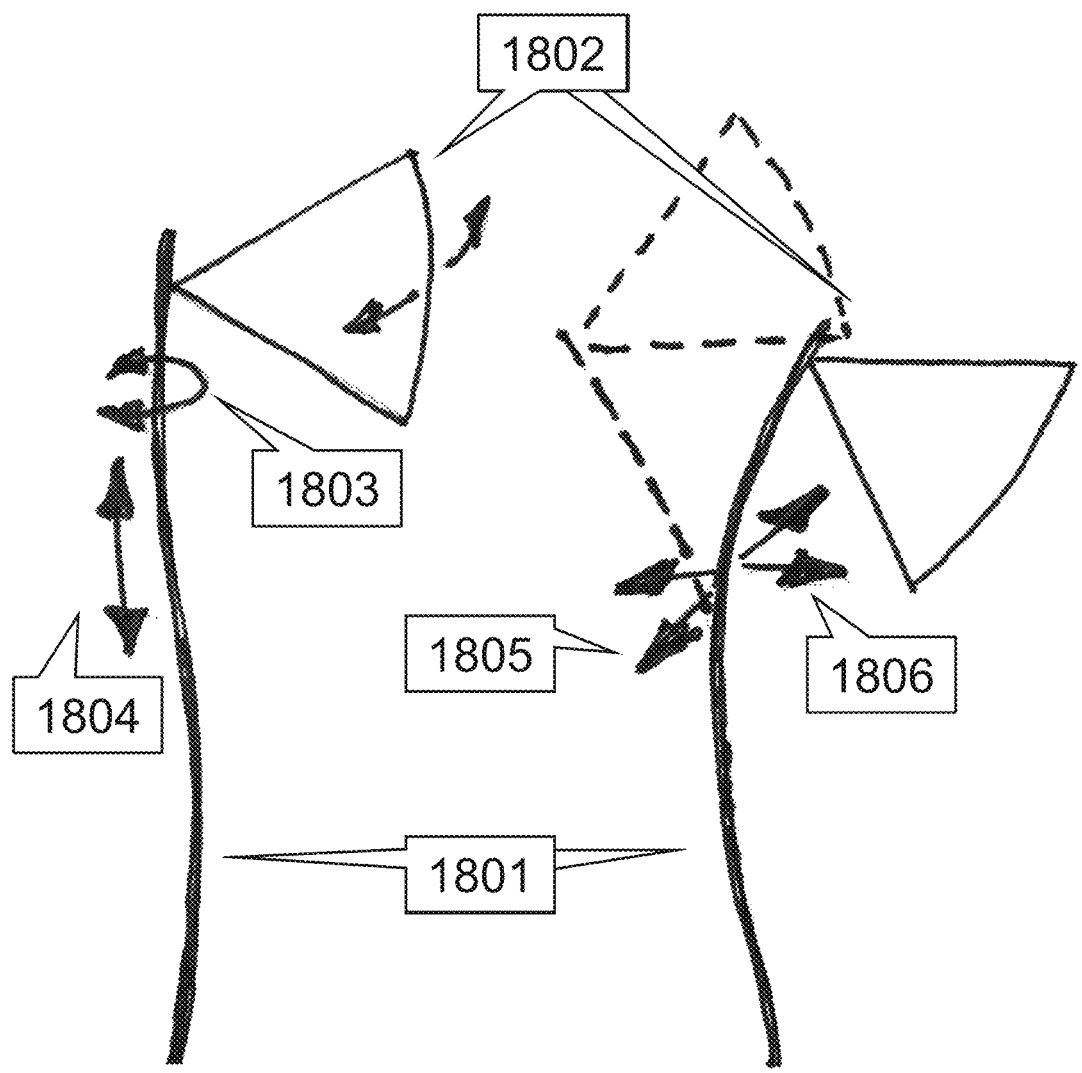
FIG. 18 illustrates possible movements to manipulate the probe to acquire an intracardiac echocardiography image.

FIG. 18 shows the ICE catheter (1801), the ICE field of view (1802) and its degrees of freedom (1803-1806). Similar to the already discussed TEE probe (FIG. 6), the ICE catheter (1801) has shaft rotation (1803), insertion depth (1804). Left-Right flex (1805) and Antero-Retro flex (1806). These are identical to the TEE probe except that the TEE can rotate its field of view (transducer angle, 604 of FIG. 6). The initial path of the catheter, which may be automatically or manually planned, will run through a blood vessels connected to the heart, and must be extended into the heart chambers. This path may be planned manually or automatically.

The present disclosure mainly describes the objects of interest as the heart. The skilled person would appreciate that this teaching can be equally extended to objects. Furthermore, the present disclosure refers to CT image dataset. The skilled person would appreciate that this teaching can be equally extended to other imaging modalities, for instance rotational angiography, MRI, SPECT, PET, 3D Ultrasound, or the like.

Figure 12:
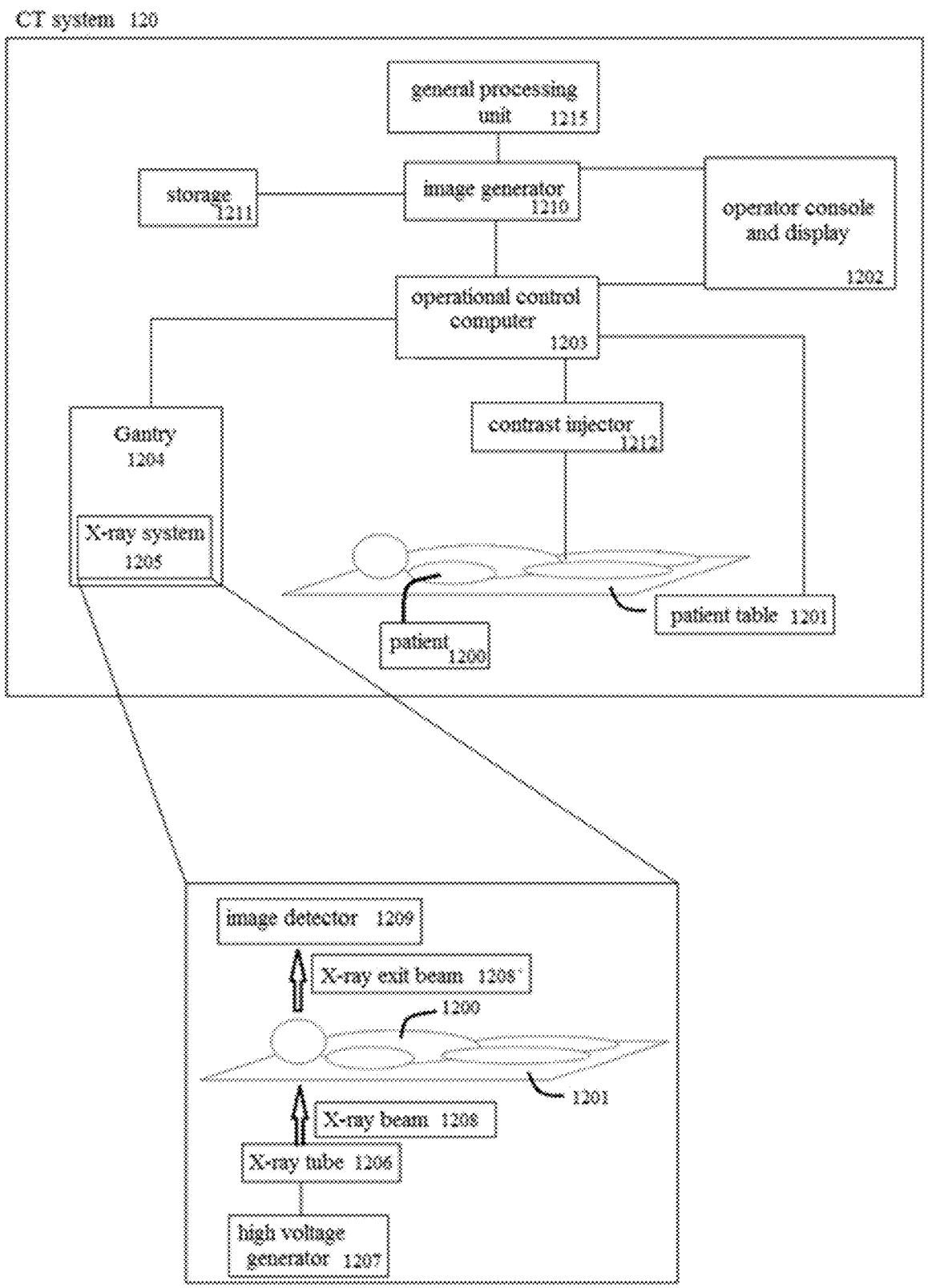
FIG. 12 shows a high-level block diagram of an example of an X-ray CT system.

The embodiment of this disclosure can be used on a standalone system or included directly in, for instance, a computed tomography (CT) system and/or a TEE or ICE imaging system and/or an X-ray system. FIG. 12 illustrates an example of a high-level block diagram of a computed tomography (CT) system. In this block diagram the embodiment is included as an example how the present embodiment could integrate in such a system.

Portions of the system (as defined by various functional blocks) may be implemented with dedicated hardware, analog and/or digital circuitry, and/or one or more processors operating program instructions stored in memory.

The most common form of computed tomography is X-ray CT, but many other types of CT exist, such as positron emission tomography (PET) and single-photon emission computed tomography (SPECT).

The CT system of FIG. 12 describes an X-ray CT system. In an X-ray CT system an X-ray system moves around a patient in a gantry and obtains images. Through use of digital processing a three-dimensional image is constructed from a large series of two-dimensional angiographic images taken around a single axis of rotation.

For a typical X-ray CT system 120 an operator positions a patient 1200 on the patient table 1201 and provides input for the scan using an operating console 1202. The operating console 1202 typically consists of a computer, a keyboard/foot paddle/touchscreen and one or multiple monitors.

An operational control computer 1203 uses the operator console input to instruct the gantry 1204 to rotate but also sends instructions to the patient table 1201 and the X-ray system 1205 to perform a scan.

Using a selected scanning protocol selected in the operator console 1202, the operational control computer 1203 sends a series of commands to the gantry 1204, the patient table 1201 and the X-ray system 1205. The gantry 1204 then reaches and maintains a constant rotational speed during the entire scan. The patient table 1201 reaches the desired starting location and maintains a constant speed during the entire scan process.

The X-ray system 1205 includes an X-ray tube 1206 with a high voltage generator 1207 that generates an X-ray beam 1208.

The high voltage generator 1207 controls and delivers power to the X-ray tube 1206. The high voltage generator 1207 applies a high voltage across the vacuum gap between the cathode and the rotating anode of the X-ray tube 1206.

Due to the voltage applied to the X-ray tube 1206, electron transfer occurs from the cathode to the anode of the X-ray tube 1206 resulting in X-ray photon generating effect also called Bremsstrahlung. The generated photons form an X-ray beam 1208 directed to the image detector 1209.

An X-ray beam 1208 consists of photons with a spectrum of energies that range up to a maximum determined by among others the voltage and current submitted to the X-ray tube 1206.

The X-ray beam 1208 then passes through the patient 1200 that lies on a moving table 1201. The X-ray photons of the X-ray beam 1208 penetrate the tissue of the patient to a varying degree. Different structures in the patient 1200 absorb different fractions of the radiation, modulating the beam intensity.

The modulated X-ray beam 1208' that exits from the patient 1200 is detected by the image detector 1209 that is located opposite of the X-ray tube.

This image detector 1209 can either be an indirect or a direct detection system.

In case of an indirect detection system, the image detector 1209 consists of a vacuum tube (the X-ray image intensifier) that converts the X-ray exit beam 1208' into an amplified visible light image. This amplified visible light image is then transmitted to a visible light image receptor such as a digital video camera for image display and recording. This results in a digital image signal.

In case of a direct detection system, the image detector 1209 consists of a flat panel detector. The flat panel detector directly converts the X-ray exit beam 1208' into a digital image signal.

The digital image signal resulting from the image detector 1209 is passed to the image generator 1210 for processing. Typically, the image generation system contains high-speed computers and digital signal processing chips. The acquired data are preprocessed and enhanced before they are sent to the display device 1202 for operator viewing and to the data storage device 1211 for archiving.

In the gantry the X-ray system is positioned in such a manner that the patient 1200 and the moving table 1201 lie between the X-ray tube 1206 and the image detector 1209.

In contrast enhanced CT scans, the injection of contrast agent must be synchronized with the scan. The contrast injector 1212 is controlled by the operational control computer 1203.

An embodiment of the present application is implemented by the X-ray CT system 120 of FIG. 12 as follows. A clinician or other user acquires a CT scan of a patient 1200 by selecting a scanning protocol using the operator console 1202. The patient 1200 lies on the adjustable table 1201 that moves at a continuous speed during the entire scan controlled by the operational control computer 1203. The gantry 1204 maintains a constant rotational speed during the entire scan Multiple two-dimensional X-ray images are then generated using the high voltage generator 1207, the X-ray tube 1206, the image detector 1209 and the digital image generator 1210 as described above. This image is then stored on the hard drive 1211. Using these X-ray images, a three-dimensional image is constructed by the image generator 1210.

The general processing unit 1215 uses the three-dimensional image to perform workflow as described by FIG. 1.

Figure 17:
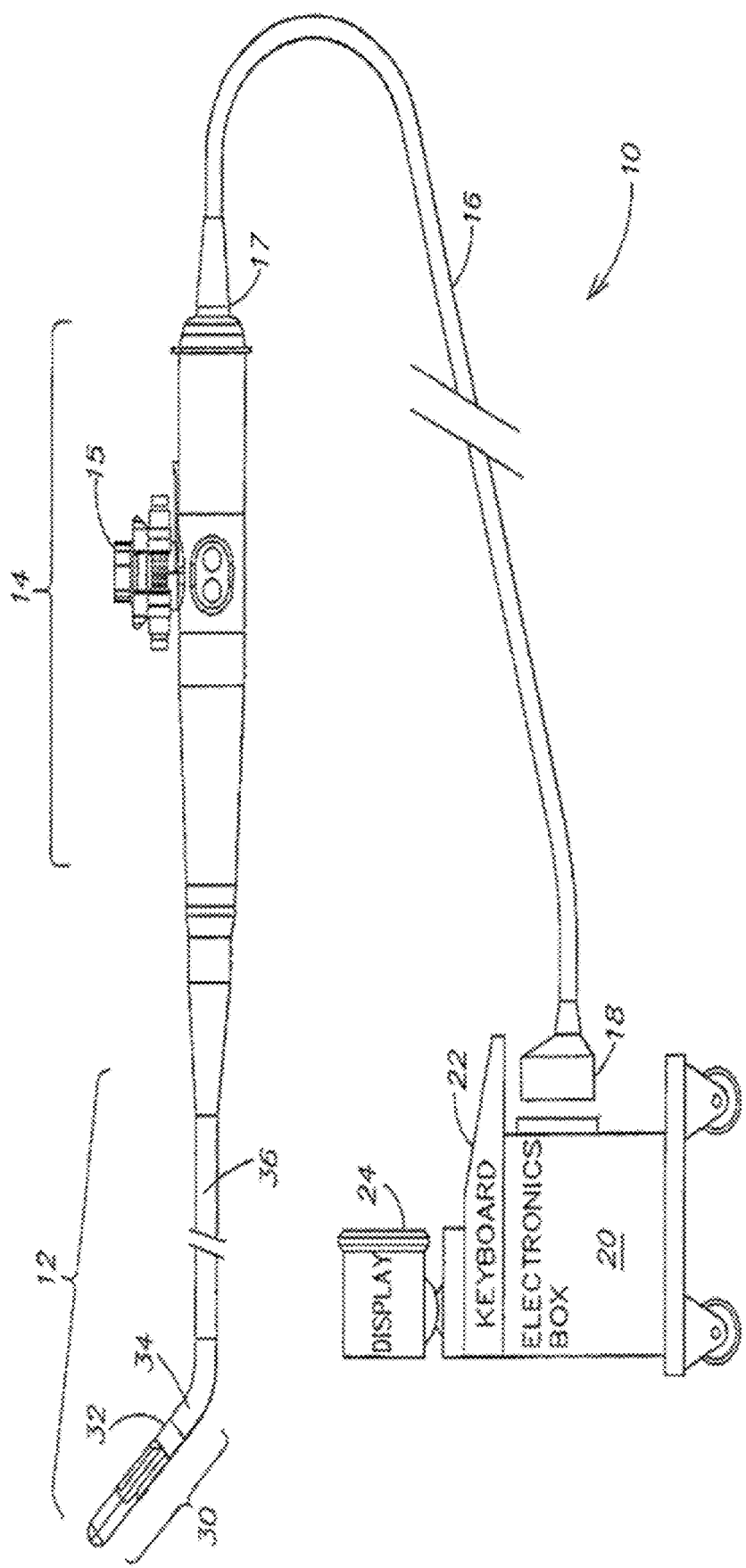
FIG. 17 illustrates an example of a TEE system.

Another embodiment of the present application is implemented by the TEE imaging system. FIG. 17 illustrates an example of a TEE system. Referring to FIG. 18, a transesophageal (TEE) imaging system (10) includes a transesophageal probe or TEE probe (12) with a probe handle (14), connected by a cable (16), a strain relief (17), and a connector (18) to an electronics box (20). The electronics box (20) is interfaced with a keyboard (22) and provides imaging signals to a video display (24). The electronics box (20) includes a transmit beamformer, a receive beamformer, and an image generator. The transesophageal probe (12) has a distal part (30) connected to an elongated semi-flexible body (36). The proximal end of elongated part (36) is connected to the distal end of probe handle (14). Distal part (30) of probe (12) includes a rigid region (32) and a flexible region (34), which is connected to the distal end of elongated body (36). Probe handle (14) includes a positioning control (15) for articulating flexible region (34) and thus orienting rigid region (32) relative to tissue of interest. Elongated semi-flexible body (36) is constructed and arranged for insertion into the esophagus. The entire insertion tube is about 110 cm long and has about 30 French in diameter.

A clinician or other user acquires a TEE scan of a patient using the TEE imaging system (10) by selecting a scanning protocol using the keyboard (22) and the transesophageal probe (12). The electronics box (20) uses the report as generated by the workflow in FIG. 1 to support the workflow as described by FIG. 13. This described embodiment can also be implemented by the ICE imaging system.

Another embodiment of the present application is implemented by the TEE imaging system. Within this embodiment the electronics box (20) uses the image data from the CT system to perform the workflow as described by FIG. 1 and/or the workflow as described by FIG. 13. This described embodiment can also be implemented by the ICE imaging system.

Another embodiment of the present application is implemented by the TEE imaging system. Within this embodiment the electronics box (20) uses the probe parameters as computed within the workflow as described by FIG. 1 and automatically sets the probe position by controlling the positioning control (15). This can be for instance performed by using electronic (servo) motor, which controls the controls on the position control (15). This described embodiment can also be implemented by the ICE imaging system.

Figure 19:
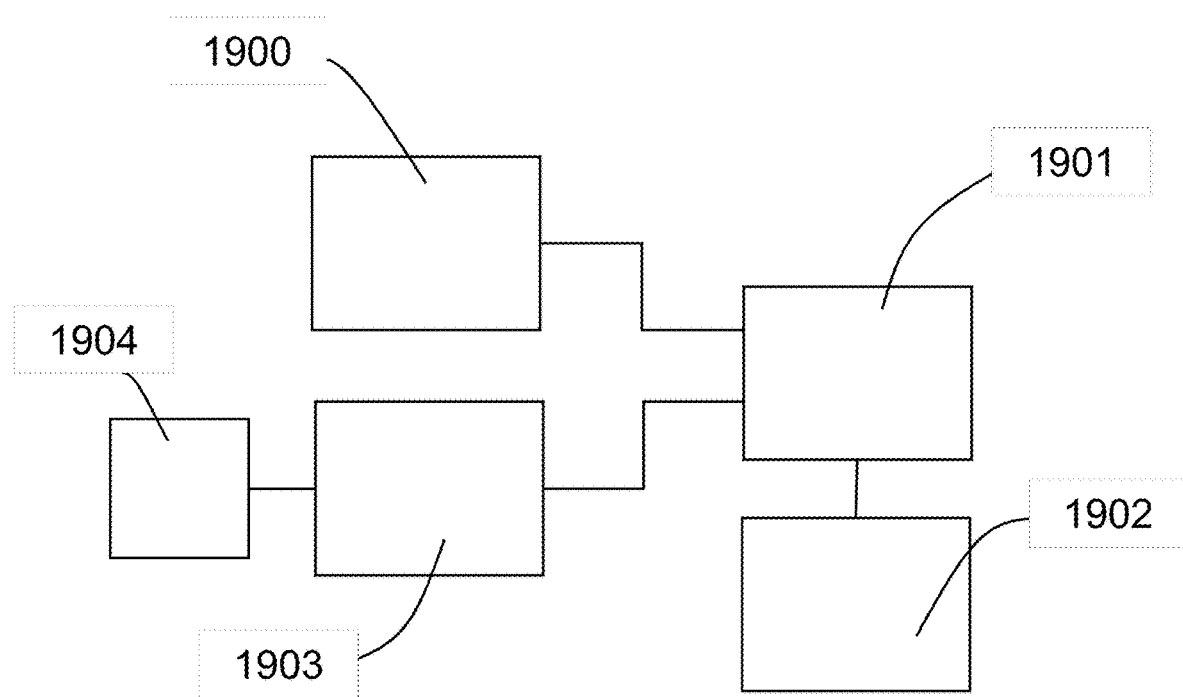
FIG. 19 illustrates an example of an integrated system including a volumetric and an intracavity imaging subsystem according to embodiments herein.

FIG. 19 shows an integrated system for planning a medical intervention on patient that involves an intracavity probe. The system includes memory 1902 configured to store an imaging dataset of a patient, and at least one processor 1901. When executing program instructions stored in the memory, the at least one processor can be configured to execute one or more steps of the method according to embodiments herein.

The system may advantageously comprise a volumetric imaging acquisition subsystem 1900 and an intracavity probe acquisition subsystem 1903. The intracavity probe acquisition subsystem 1903, for example a TEE or an intravascular system, can be configured to acquire images from an intracavity probe 1904 interfaced thereof, while the volumetric imaging acquisition subsystem 1900 can be configured to acquire the imaging dataset of the patient using, for example, a volumetric imaging modality selected from the group consisting of X-ray CT imaging, rotational angiography, MRI, SPECT, PET, three-dimensional ultrasound, and the like The at least one processor 1901 may be advantageously configured to:

- store data representing at least one virtual intracavity image and corresponding probe parameters of the intracavity probe as part of a plan for the medical intervention;
- with the intracavity probe located and oriented to correspond to certain probe parameters stored as part of the plane, acquire a live intracavity image by operation of the intracavity probe; and
- generate a display that displays together a virtual intracavity image stored as part of the plan and the live intracavity image probe acquired by operation of the intracavity probe There have been described and illustrated herein several embodiments of a method and system for intervention planning.

While particular embodiments of the present application have been described, it is not intended that the present application be limited thereto, as it is intended that the present application be as broad in scope as the art will allow and that the specification be read likewise.

For example, the data processing operations can be performed offline on images stored in digital storage, such as a picture archiving and communication system (PACS) commonly used in the medical imaging arts. It will therefore be appreciated by those skilled in the art that yet other modifications could be made to the provided application without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art.

Similarly, any necessary files for performing the functions attributed to the computers, servers or other network devices may be stored locally and/or remotely, as appropriate.

Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above.

The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser.

It should be appreciated that alternate embodiments may have numerous variations from that described above. For example, customized hardware might also be used, and/or particular elements might be implemented in hardware, software (including portable software, such as applets) or both.

Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the present application as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the present application to the specific form or forms disclosed, but on the contrary, the intention is to cover all modifications, alternative constructions and equivalents falling within the spirit and scope of the present application, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening.

Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members.

Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the present application. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein.

Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

What is claimed is:

1. A method of planning a medical intervention on patient that involves an intracavity probe, the method comprising:
providing or accessing an imaging dataset of the patient;
determining location of at least one anatomical structure in the imaging dataset;
determining an intracavity path of the intracavity probe;
selecting a view-type from a defined set of view-types;
determining probe parameters that represent location and orientation of the intracavity probe based on i) a pre-defined set of rules for the selected view-type, ii) the intracavity path, and iii) the location of at least one anatomical structure in the imaging dataset, wherein the set of rules is adapted to determine probe parameters where the at least one anatomical structure or landmark is positioned in a field of view of the intracavity probe;
determining a virtual field of view of the intracavity probe based on the probe parameters; and
rendering for display a virtual intracavity image based on the imaging dataset of the patient and the virtual field of view of the intracavity probe.

2. A system for planning a medical intervention on patient that involves an intracavity probe, the system comprising:
memory configured to store an imaging dataset of a patient; and
at least one processor that, when executing program instructions stored in the memory, is configured to perform the method of claim 1.

3. A system according to claim 2, further comprising:
an imaging acquisition subsystem and an intracavity probe such as a TEE probe or ICE probe, the imaging acquisition subsystem being configured to acquire images from the intracavity probe.

4. A system according to claim 3, wherein the at least one processor is configured to:
store data representing at least one virtual intracavity image and corresponding probe parameters of the intracavity probe as part of a plan for the medical intervention;
with the intracavity probe located and oriented to correspond to certain probe parameters stored as part of the plan, acquire a live intracavity image by operation of the intracavity probe; and
generate a display that displays together a virtual intracavity image stored as part of the plan and the live intracavity image.

5. A system according to claim 2, further comprising:
an imaging acquisition subsystem that is configured to acquire the imaging dataset of the patient.

6. A system according to claim 5, wherein:
the imaging acquisition subsystem uses a volumetric imaging modality selected from the group consisting of X-ray CT imaging, rotational angiography, MRI, SPECT, PET, three-dimensional ultrasound, and the like.

7. A method according to claim 1, wherein:
the intracavity path is determined based on segmentation of at least one cavity structure selected from the group consisting of: esophagus, rectum, vagina, vessel, heart atrium, or heart ventricle.

8. A method according to claim 1, wherein:
the probe parameters are selected from a group consisting of: shaft insertion depth, shaft rotation, probe rotation angle, shaft bending anterior-posterior angle, shaft bending left-right angle.

9. A method according to claim 1, wherein:
the orientation of the intracavity probe is defined by a view direction and a plane orientation.

10. A method according to claim 1, wherein:
the intracavity probe comprises a TEE probe or ICE probe.

11. A method according to claim 1, further comprising:
selectively adjusting probe parameters of the intracavity probe;
recalculating a virtual field of view of the probe based on the adjusted probe parameters; and
rendering for display another virtual intracavity image based on the imaging dataset of the patient and the recalculated virtual field of view of the probe.

12. A method according to claim 1, further comprising:
selectively storing data representing the virtual intracavity image and the corresponding probe parameters as part of a plan.

13. A method according to claim 1, wherein:
the imaging dataset of the patient is acquired using a volumetric imaging modality selected from the group consisting of X-ray CT imaging, rotational angiography, MRI, SPECT, PET, three-dimensional ultrasound, and the like.

14. A method according to claim 1, wherein:
the probe parameters are determined by evaluation of cost function expressed by the pre-defined set of rules for the selected view-type and the intracavity path and the location of at least one anatomical structure in the imaging dataset.

15. A method according to claim 1, wherein:
the location of at least one anatomical structure in the imaging dataset is determined by automatic or semi-automatic segmentation of the imaging dataset.

16. A method according to claim 1, wherein:
the location of at least one anatomical structure in the imaging dataset is determined by manual segmentation of the imaging dataset.

17. A method according to claim 1, wherein:
the at least one anatomical structure is selected from the group consisting of: Mitral annulus, Tricuspid annulus, Aortic annulus, Pulmonary valve, Fossa Ovalis, Apex, Lower Mitral Commissure, Upper Mitral Commissure, Atrial appendage, SVC (Superior Vena Cava), IVC (Inferior Vena Cava).

18. A method according to claim 1, wherein:
the defined set of view-types include view types selected from the group consisting of: two chamber, four chamber, BiCaval, Mitral Commissural, Mitral Short Axis.

* * * * *